(12) United States Patent
Morris et al.

(10) Patent No.: US 6,596,514 B2
(45) Date of Patent: Jul. 22, 2003

(54) EXPRESSION AUGMENTING SEQUENCE ELEMENTS (EASE) FOR EUKARYOTIC EXPRESSION SYSTEMS

(75) Inventors: Arvia E. Morris, Seattle, WA (US); James N. Thomas, Redmond, WA (US)

(73) Assignee: Immunex Corporation, Seattle, WA (US)

(*) Notice: Subject to any disclaimer, the term of this patent is extended or adjusted under 35 U.S.C. 154(b) by 0 days.

(21) Appl. No.: 09/973,928

(22) Filed: Oct. 9, 2001

(65) Prior Publication Data

US 2003/0008345 A1 Jan. 9, 2003

Related U.S. Application Data

(63) Continuation-in-part of application No. 09/660,299, filed on Sep. 12, 2000, now Pat. No. 6,309,841, which is a continuation-in-part of application No. 09/435,377, filed on Nov. 5, 1999, now Pat. No. 6,312,951, which is a continuation of application No. 08/785,150, filed on Jan. 13, 1997, now Pat. No. 6,027,915, which is a continuation-in-part of application No. 08/586,509, filed on Jul. 11, 1996, now abandoned.
(60) Provisional application No. 60/186,537, filed on Mar. 2, 2000.

(51) Int. Cl.$^7$ ................................................ C12P 12/02
(52) U.S. Cl. .................... 435/69.1; 435/358; 435/320.1; 536/24.1
(58) Field of Search ............................ 435/69.1, 358, 435/320.1; 536/24.1

(56) References Cited

U.S. PATENT DOCUMENTS

| | | | |
|---|---|---|---|
| 5,081,018 A | | 1/1992 | Grummt et al. |
| 6,027,915 A | * | 2/2000 | Morris et al. ............... 435/69.1 |
| 6,309,841 B1 | * | 10/2001 | Morris et al. ................. 435/6 |
| 6,312,951 B1 | * | 11/2001 | Morris et al. ............... 435/358 |

FOREIGN PATENT DOCUMENTS

EP          0306848         3/1989

OTHER PUBLICATIONS

Beitel, L., et al., "Sequence requirements for the stimulation of gene amplification by a mammalian genomic element," *Gene* 102:149–156, 1991.
Gasser, S. and Laemmli, U., "A glimpse at chromosomal order," *Trends Genet* 3:16–22, 1987.
Grosveld, F., et al., "Position–independent, high–level expression of the human β–globin gene in transgenic mice," *Cell* 51: 975–985, 1987.
Hemann, C., et al., "High–copy expression vector based on amplification–promoting sequences," *DNA Cell Biol* 13(4):437–445, 1994.
Holst, A., et al., "Murine genomic DNA sequences replicating autonomously in mouse L cells," *Cell* 52:355–365, 1988.

Kaufman, R., et al., "Improved vectors for stable expression of foreign genes in mammalian cells by use of the untranslated leader sequence from EMC virus," *Nucleic Acids Res* 19(16):4485–4490, 1991.
Kellum, R. and Schedl, P., "A position–effect assay for boundaries of higher order chromosomal domains," *Cell* 64:941–950, 1991.
Klehr, D., et al., "Scaffold–attached regions from the human interferon β domain can be used to enhance the stable expression of genes under the control of various promoters," *Biochemistry* 30 : 1264–1270, 1991.
McArthur, J. and Stanners, C., "A genetic element that increases the frequency of gene amplification," *J Biol Chem* 266(9):6000–6005, 1991.
McArthur, J., et al., "Elements which stimulate gene amplification in mammalian cells: role of recombinogenic sequences/structures and transcriptional activation," *Nucleic Acids Res* 19(9):2477–2484, 1991.
McBratney, S., et al., "Internal initiation of translation," *Curr Opin Cell Biol* 5: 961–965, 1993.
Meyer, J., et al., "Inhibition of HIV–1 replication by a high–copy–number vector expressing antisense RNA for reverse transcriptase," *Gene* 129:263–268, 1993.
Phi–Van, L., et al., "The chicken lysozyme 5' matrix attachment region increases transcription from a heterologous promoter in heterologous cells and dampens position effects on the expression of transfected genes," *Mol Cell Biol* 10(5): 2302–2307, 1990.
Stolzenburg, F., et al., "Structural homologies and functional similarities between mammalian origins of replication and amplification promoting sequences," *Chromosoma* 103:209–214, 1994.
Wegner, M., et al., "An amplification–promoting sequence from mouse genomic DNA: interaction with a trans–acting factor that also affects gene expression," *DNA Cell Biol* 9(5): 311–321, 1990.
Wegner, M., et al., "Interaction of a protein with a palindromic sequence from murine rDNA increases the occurrence of amplification–dependent transformation in mouse cells," *J Biol Chem* 265(23):13925–13932, 1990.
Wegner, M., et al., "Cis–acting sequences from mouse rDNA promote plasmid DNA amplification and persistence in mouse cells: implication of HMG–1 in their function," *Nucleic Acids Res* 17(23):9909–9932,1989.
Weidle, U., et al., "A new expression system for mammalian cells based on putative replicator sequences of the mouse and a truncated thymidine kinase gene," *Gene* 73: 427–437, 1988.
Weidle, U., et al., "Amplified expression constructs for human tissue–type plasminogen activator in Chinese hamster ovary cells: instability in the absence of selective pressure," *Gene* 66: 193–203, 1988.

* cited by examiner

Primary Examiner—James Ketter
(74) Attorney, Agent, or Firm—Christine M. Bellas; Kathleen Fowler

(57) ABSTRACT

There are disclosed nucleotide sequences which can improve expression of recombinant proteins two- to eightfold in stable cell pools when present in an expression vector.

16 Claims, 6 Drawing Sheets

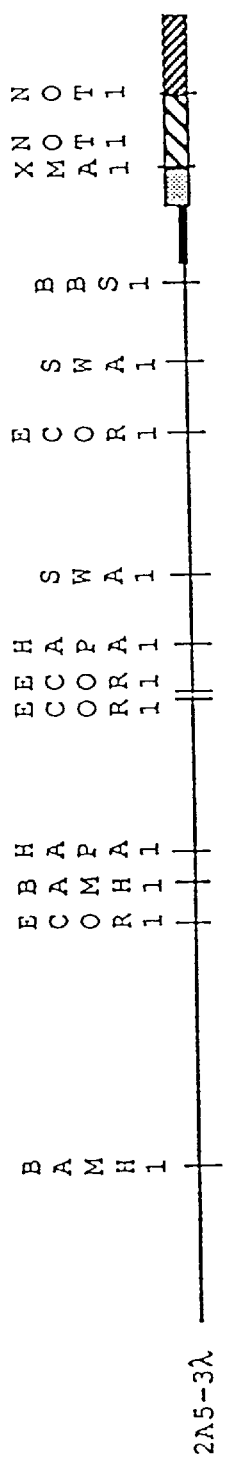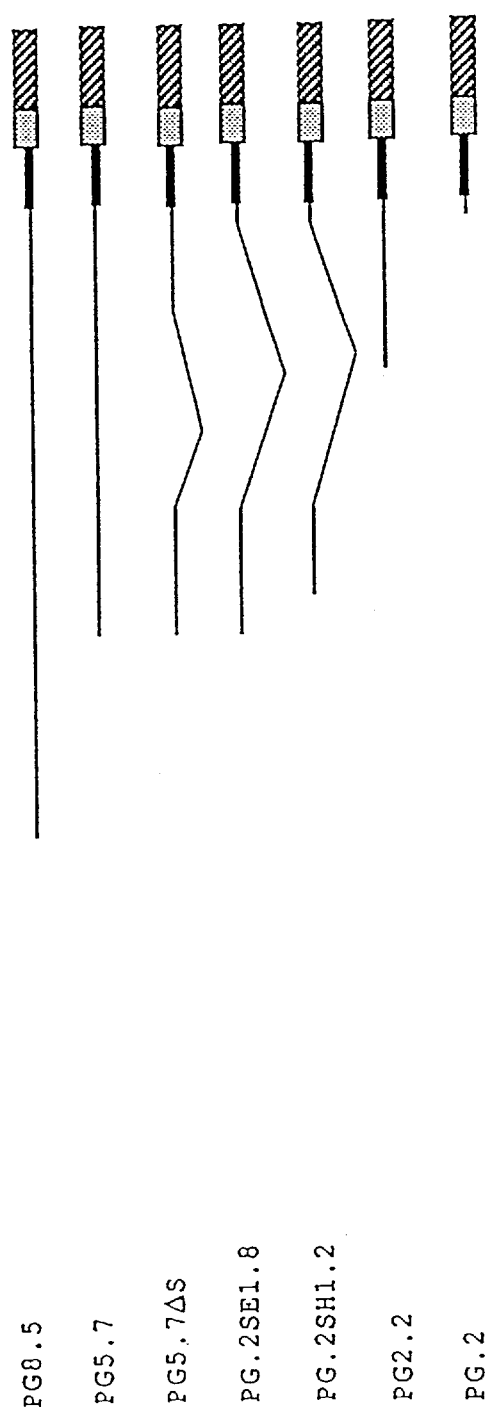
FIGURE 1A
FIGURE 1B

FIGURE 3

```
human HMG-I    1  MSESSSKSSQPLASKQEKDGTEKRGRGRPRKQPPVSRGTALVGSQKEPSE  50
CHO HMG-I      1  MSESGSKSSQPLASKQEKDGTEKRGRGRPRKQPPVSRGTALVGSQKEPSE  50
CHO HMG-Y      1  MSESGSKSSQPLASKQEKDGTEKRGRGRPRKQPP.............KEPSE  39
murine HMG-Y   1  MSESGSKSSQPLASKQEKDGTEKRGRGRPRKQPP.............KEPSE  39 human HMG-I   51  VPTPKRPRGRPKGSKNKGAAKTRKTTTTPGRKPRGRPKKLEKEEEGISQ  100
CHO HMG-I     51  VPTPKRPRGRPKGSKNKGAAKTRKATTAPGRKPRGRPKKLEKEEEGISQ  100
CHO HMG-Y     51  VPTPKRPRGRPKGSKNKGAAKTRKATTAPGRKPRGRPKKLEKEEEGISQ  100
murine HMG-Y  40  VPTPKRPRGRPKGSKNKGAAKTRKVTTAPGRKPRGRPKKLEKEEEGISQ  89 human HMG-I  101  ESSEEEQ  107
CHO HMG-I    101  ESSEEEQ  107
CHO HMG-Y    101  ESSEEEQ  107
murine HMG-Y  90  ESSEEEQ   96
```

FIGURE 5

A
B
FIGURE 6

EXPRESSION AUGMENTING SEQUENCE ELEMENTS (EASE) FOR EUKARYOTIC EXPRESSION SYSTEMS

CROSS-REFERENCE TO RELATED APPLICATIONS

This application is a continuation-in-part of U.S. application Ser. No. 09/660,299, filed Sep. 12, 2000, now U.S. Pat. No. 6,309,841, which claims benefit under 35 U.S.C. §119 (e) of U.S. Provisional Patent Application No. 60/186,537, filed Mar. 2, 2000; and which is a continuation-in-part of U.S. application Ser. No. 09/435,377, filed Nov. 5, 1999, now U.S. Pat. No. 6,312,951; which is a continuation of U.S. application Ser. No. 08/785,150, filed Jan. 13, 1997, now U.S. Pat. No. 6,027,915; which is a continuation-in-part of U.S. application Ser. No. 08/586,509, filed Jan. 11, 1996, now abandoned.

BACKGROUND OF THE INVENTION

1. Technical Field of the Invention

The present invention relates to DNA sequence elements that augment the expression of recombinant proteins in eukaryotic cells.

2. Description of the Related Art

The development of expression systems for production of recombinant proteins is important for developing a source of a given protein for research or therapeutic use. Expression systems have been developed for both prokaryotic cells, such as E. coli, and for eukaryotic cells, which includes both yeast (i.e., Saccharomyces, Pichia and Kluyveromyces spp) and mammalian cells. Expression in mammalian cells is often preferred for manufacturing of therapeutic proteins, since post-translational modifications in such expression systems are more likely to resemble those found in a mammal than the type of post-translational modifications that occur in microbial (prokaryotic) expression systems.

Transcription of eukaryotic genes is regulated by a variety of cis- and trans-acting regulatory elements (reviewed by Dillon and Grosveld, Trends Genet. 9:134; 1993). Two of the best characterized cis elements are promoters and enhancers. Promoters are DNA sequences immediately 5' to the coding sequence of the gene and encompass multiple binding sites for trans-acting transcription factors, forming the basal transcription apparatus. Enhancers are also composed of multiple binding sites for trans-acting transcription factors but can be found far up stream or down stream of coding sequences or even within introns. These elements can also act in an orientation independent manner. The activities of promoters and enhancers can be detected in transient expression systems and contain elements which may or may not be tissue specific; they are vulnerable to position effects when studied in stable cell lines or transgenic animals.

Another category of cis- regulatory elements are ones which are believed to regulate the chromatin structure including, locus control regions (LCR) (Grosveld F., et al., Cell 51:975, 1987), matrix attachment regions (MAR; Phi-Van et al., Mol Cell Biol 10:2302; 1980), scaffold attachment regions (SAR; Gasser and Laemmli, Trends Genet 3:16, 1987), and insulator elements (Kellum and Schedl, Cell 64:941, 1991). These elements are similar to enhancers in that they are able to act over long distances, but are unique in that their effects are only detectable in stably transformed cell lines or transgenic animals. LCRs are also dissimilar to enhancers in that they are position and orientation dependent, and are active in a tissue specific manner. In addition, LCR and SAR sequences are characterized by A boxes, T boxes and topoisomerase II sites, which are not typically found in enhancer or promoter sequences. (Gasser and Laemmli, supra; Klehr D., et al., Biochemistry 30:1264, 1991).

Internal ribosome entry sites (IRES) are another type of regulatory element that can be found in several viruses and cellular RNAs (reviewed in McBratney et. al. Current Opinion in Cell Biology 5:961, 1993). IRES are useful in enhancing translation of a second gene product in a bicistronic eukaryotic expression cassette (Kaufman R. J., et al., Nucleic Acids Res 19:4485, 1991).

Another type of regulatory element is the HMG-I(Y) family. The HMG-I(Y) family of "high mobility group" nonhistone chromatin proteins are founding members of a new category of mammalian gene trans-regulatory proteins called "architectural transcription factors" (Grosschedl, et al., Trends Genet. 10:94–100 (1994); Bustin and Reeves, Prog. Nucleic Acid Res. Mol. Biol. 54:35–100 (1996)). In contrast to most transcription factors that bind to specific nucleotide recognition sites in the major groove, architectural transcription factors are characterized by their ability to recognize and modulate DNA and chromatin structure and typically bind to the minor groove of DNA substrates. The HMG-I(Y) family consists of three closely related proteins, HMG-I, HMG-Y and HMG-IC. Each possess three independent DNA-binding domains called "A.T-hooks" because of their ability to recognize and bind to the narrow minor groove of stretches of A.T-rich nucleotides. A.T-hooks also recognize distorted DNA structures such as those present on synthetic four-way junctions (Hill and Reeves, Nucleic Acids Res. 25:3523–31 (1997)), Hill et al., Nucleic Acids Res. 27:2135–44 (1999)), supercoiled plasmids (Nissen and Reeves, J Biol. Chem. 270:4344–4360 (1995)), and the surface of nucleosome core particles (Reeves and Wolffe, Biochemistry 35:5063–74 (1996)).

Several vectors are available for expression in mammalian hosts, each containing various combinations of cis- and in some cases trans- regulatory elements to achieve high levels of recombinant protein in a minimal time frame. However, despite the availability of numerous such vectors, the level of expression of a recombinant protein achieved in mammalian systems is often lower than that obtained with a microbial expression system. Moreover, developing a transformed cell line that expresses high levels of a desired protein often requires time consuming cloning and amplification. Accordingly, there is a need in the art to refine and improve expression in mammalian cells, and to identify elements that can augment expression of recombinant proteins and facilitate the use of mammalian cells in recombinant protein production.

SUMMARY OF THE INVENTION

Novel regulatory sequences, expression augmenting sequence elements (EASE), that facilitate high expression of recombinant proteins in mammalian host cells in a short time period, are disclosed. One embodiment of the invention is an expression augmenting sequence element (EASE), that facilitates high expression of recombinant proteins in mammalian host cells in a short time period, which is not active in transient expression systems, does not exhibit characteristics of DNAs that encode a protein, and does not exhibit nucleotide sequence characteristics found in LCR, MAR or SAR such as clusters of A and T boxes and topoisomerase II sites. The instant invention may contain certain putative MAR as defined by Singh et al. (Nucleic Acids Res.

25:1419–25(1997). A preferred embodiment of the invention is an EASE that was obtained from Chinese hamster ovary (CHO) cell genomic DNA, proximal to a unique integration site for a recombinant mammalian protein.

In a preferred embodiment of the invention, the EASE is selected from the group consisting of DNAs comprising nucleotides 46 through 14507 of a nucleotide sequence set forth in SEQ ID NO:1, nucleotides 5980 through 14507 of a nucleotide sequence set forth in SEQ ID NO:1, nucleotides 8671 through 14507 of the nucleotide sequence set forth in SEQ ID NO:1, nucleotides 8673 through 12274 of the nucleotide sequence set forth in SEQ ID NO:1, nucleotides 8671 through 10516 ligated to nucleotides 12592 through 14507 of the nucleotide sequence set forth in SEQ ID NO:1, nucleotides 8671 through 10516 ligated to nucleotides 14291 through 14507 of the nucleotide sequence set forth in SEQ ID NO:1, nucleotides 9277 through 10516 ligated to nucleotides 14291 through 14507 of the nucleotide sequence set forth in SEQ ID NO:1, fragments of the foregoing DNAs that have expression augmenting activity, DNAs complementary to the forgoing DNAs, and combinations of the foregoing DNAs that have expression augmenting activity.

Particularly preferred embodiments comprise EASE sequences from the box III region, for example, the present invention provides EASE sequences selected from the group consisting of DNAs comprising nucleotides 11538 through 12165 of a nucleotide sequence set forth in SEQ ID NO: 1, nucleotides 11538 through 11692 of a nucleotide sequence set forth in SEQ ID NO:1, and nucleotides 11813 through 12165 of a nucleotide sequence set forth in SEQ ID NO:1, as well as a ligated form of nucleotides 11538 through 11692 and nucleotides 11813 through 12165, which is herein referred to as EASE45. Additionally, EASE sequences may be selected from the group consisting of DNAs comprising nucleotides 11538 through 11760 of a nucleotide sequence set forth in SEQ ID NO:1, and nucleotides 11899 through 12165 of a nucleotide sequence set forth in SEQ ID NO:1, as well as a ligated form of nucleotides 11538 through 11760 and nucleotides 11899 through 12165, which is herein referred to as EASE12. In yet further embodiments, EASE sequences may comprise nucleotides 11673 through 12165 of a nucleotide sequence set forth in SEQ ID NO:1, which is herein referred to as EASE3. Of course, it is understood that any or all of the aforementioned EASE sequences may be used alone or in any combination.

Expression vectors comprising the novel EASE are able to transform CHO cells to high expression of recombinant proteins. Thus, another embodiment of the invention is an expression vector comprising an EASE. In a preferred embodiment, the expression vector further comprises an eukaryotic promoter/enhancer driving the expression of a protein of interest. In a most preferred embodiment, the expression vector consists of a bicistronic plasmid wherein a first exon encodes the gene of interest and a second exon encodes an amplifiable dominant selectable marker. A preferred marker is dihydrofolate reductase (DHFR); other amplifiable markers are also suitable for use in the inventive expression vectors. The expression vector may further comprise an IRES sequence between the two exons.

Mammalian host cells can be transformed with the inventive expression vectors, and will produce high levels of recombinant protein in a short period of time. Accordingly, another embodiment of the invention provides a mammalian host cell transformed with the inventive expression vector. In a most preferred embodiment, the host cells are CHO cells.

The invention also provides a method for obtaining a recombinant protein, comprising transforming a host cell with an inventive expression vector, culturing the transformed host cell under conditions promoting expression of the protein, and recovering the protein. In a preferred application of this invention, transformed host cell lines are selected with two selection steps, the first to select for cells expressing the dominant amplifiable marker, and the second step for high expression levels and/or amplification of the marker gene as well as the gene of interest. In a most preferred embodiment, the selection or amplification agent is methotrexate, an inhibitor of DHFR that has been shown to cause amplification of endogenous DHFR genes and transfected DHFR sequences.

Moreover, the invention provides a method of identifying additional expression augmenting sequence elements, for example, from other transformed cell lines. Such cell lines will exhibit high levels of expression that are not attributable to high gene copy number. The inventive techniques will be useful in identifying and isolating such EASE, as well as EASE present in non-transformed cells (for example, by hybridization studies or sequence analysis).

Further, high levels of EASE activity have been connected to sequences containing higher numbers of HMGI-(Y) binding sites. Thus, this invention provides a method of determining expression augmenting sequence elements by identifying sequences which contain high levels of HMGI-(Y) binding sites.

BRIEF DESCRIPTION OF THE DRAWINGS

FIG. 1A and 1B. Inserts of various lengths, derived from 2A5-3 CHO genomic DNA. FIG. 1A is a restriction map of the TNFrFc integration site cloned into a cloning vector, λFixII, as described in Example 1; restriction sites used for subcloning are indicated. The thin line corresponds to CHO genomic DNA. The thick black line is the CMV promoter, the dotted box is the adenovirus tripartite leader sequence, the left hatched boxes are the TNFrFc coding region and the smaller hatching is the DHFR-encoding sequence.

The CHO genomic DNA insert in FIG. 1A corresponds to nucleotides 46 through 14507 of SEQ ID NO:1. FIG. 1B summarizes inserts cloned into pGEM1, derived from the phage clone represented in FIG. 1A, as described in Example 6. Relative to SEQ ID NO:1, the insert in PG8.5 corresponds to nucleotides 5980 through 14507; that in PG5.7 corresponds to nucleotides 8671 through 14507; that in PG5.7ΔS corresponds to nucleotides 8671 through 10516 ligated to nucleotides 12592 through 14507; that in PG.2SE1.8 corresponds to nucleotides 8671 through 10516 ligated to nucleotides 14291 through 14507; that in PG.2SH1.2 corresponds to nucleotides 9277 through 10516 ligated to nucleotides 14291 through 14507; that in PG2.2 corresponds to nucleotides 12269 through 14507; and the insert in PG.2 corresponds to nucleotides 14291 through 14507.

FIG. 3. Sequence of EASE element containing box II and box III of HMG binding sites. Boxes II and III are depicted by boxed regions. The putative HMG-I(Y) binding sites are indicated by bold highlight. Probe 1 used for the gel shift assay includes nucleotides 10446–10719. Probe 2 used for the gel shift assay includes nucleotides 11106–11364. Probe 3 used for the gel shift assay includes nucleotides 11456–11728. The putative MAR includes nucleotides 11927–12301.

FIG. 5. Comparison of human HMG-I, CHO HMG-I, HMG-Y and murine HMG-Y amino acid sequences. The CHO and murine HMG-Y amino acid sequences are identical except at position 75. The bold amino acids (T53 and T78) were shown to be phosphorylated by cdc2 kinase (Nissen et al., *J. Biol. Chem.* 266:19945–19952 (1991)). Underlined amino acids are located in the DNA binding domains. Italicized amino acids are those found in the HMG-I protein but not in HMG-Y.

FIG. 6. HMG-I(Y) supershift assays. Black dots indicate the position of the unbound probe. Triangles indicate position of probe complexed with either recombinant HMG-I (rhuHMG-I) (FIG. 6A) or acid soluble nuclear proteins from CHO cells (CHO-HMG ext) (FIG. 6B). The star indicates the position of bands supershifted with HMG-I(Y) antibody.

DETAILED DESCRIPTION OF THE INVENTION

Figure 2:
FIG. 2. Diagram of 5.0 kb region of CHO genomic DNA with clusters of HMG-I(Y) binding sites depicted (nucleotides 8671 to 13751 of SEQ ID NO:1). The clusters correspond to nucleotides 9102 to 9703 for box I according to the numbering system in GenBank sequence number AF193761 (nucleotides 9147–9748 of SEQ ID NO:1); nucleotides 10,011 to 10,702 for box II (nucleotides 10056–10747 of SEQ ID NO:1); nucleotides 11,493 to 12,120 for box III (nucleotides 11538–12165 of SEQ ID NO:1); nucleotides 12,250 to 12,752 for box IV (nucleotides 12295–12797 of SEQ ID NO:1), and nucleotides 13,080 to 13,706 for box V (nucleotides 13125–13751 of SEQ ID NO:1).

We have identified novel sequence elements that can improve expression of reporter proteins two to eight fold in stable cell pools when inserted in an expression vector. One such sequence element was identified by cloning the integration site of a unique expression cassette encoding recombinant dimeric Tumor Necrosis Factor receptor/immunoglobulin Fc fusion protein (TNFrFc) from genomic DNA of a cell line expressing this protein at a high level. The inventive sequence elements appear to encode a novel function, since the expression enhancing activity does not behave like previously characterized cis-acting elements such as promoters, enhancers, locus control regions, scaffold attachment regions or matrix attachment regions. In addition the sequence elements do not appear to contain any open reading frames (ORFs), making it unlikely that they encode a novel trans-activator protein. We refer to these novel sequence elements as "expression augmenting sequence elements" (EASE).

PHYSICAL AND FUNCTIONAL CHARACTERIZATION OF EASE

EASE activity was identified in 14.5 kb of CHO genomic DNA 5 ' to a unique integration site of TNFrFc encoding sequences from the genome of a cell line expressing this protein at a high level (referred to as 2A5-3). The 14.5 kb of CHO EASE contains clusters of potential HMG-I(Y) binding sites (FIG. 2, boxes 1-V), which are suspected of being involved in the mechanism of action of the EASE DNA. One potential mechanism of action of EASE is increasing the rate of amplification of integrated plasmid in the presence of MTX. Breakage-fusion-bridge cycles are thought to play a role in DNA amplification (Wintersberger, E. *Chromosoma* 103:73–81(1994); DiLeonardo et al., *On Quant. Biol.* 58:655–67 (Cold Spring Harbor Symp.(1993))). HMG-I(Y) proteins are known to unwind DNA; thus, unwound DNA containing many HMG-I(Y) binding sites could be more vulnerable to single strand breaks. After the initial breaks have occurred, HMG-I(Y) proteins could facilitate healing of the broken ends by bending the DNA, enabling two broken ends to fuse in the breakage-fusion-bridge cycles. HMG-I(Y) is also know to bind to unusual DNA structures such as cruciform DNA; therefore, HMG-I(Y) also may play a role in resolving any unusual structures that may arise during the amplification process.

The binding of EASE specifically to CHO HMG-I(Y) proteins was shown using electrophoretic mobility shift assay as well as by a comparison of human, murine and hamster HMG-I(Y) amino acid sequences by RT-PCR (Examples 15 and 16). The predicted amino acid sequences for hamster, human and mouse are compared in FIG. 5. There is remarkable sequence homology between the human and rodent sequences with only three variable amino acids located at positions 5, 75 and 78. The three DNA binding domains in the hamster and mouse molecules are identical and only the third binding domain varies from the human sequence at the first amino acid position T to A. This difference in sequence suggests that the human and rodent have evolved different pathways for regulating HMG-I(Y) in rodent and humans since the T in the human sequence is the site of phosphorylation by cdc2 kinase. The core palindrome PRGRP in rodent and human are conserved. This palindrome is involved with DNA binding [Reeves et al., *J. Biol. Chem.* 265:8573–8582 (1990)]. Since the DNA binding regions in the hamster and human proteins are so similar and the purified human HMG-I protein gives the same band shift pattern as the crude CHO nuclear lysates, the banding pattern in the CHO lysates was probably due to specific binding of hamster HMG-I(Y) to probes 1 and 3, as described in Example 15.

Thus, in one embodiment of the instant invention, expression augmenting sequence elements may be identified by identifying regions of genomic DNA which contain high levels of HMGI-(Y) binding sites, cloning the regions from the cell line, and determining if the cloned sites exhibit expression augmenting activity.

In addition to the consensus HMG-I(Y) DNA binding sites, two potential matrix attachment regions (MAR) have been located within the 14.5 kb EASE. The first was identified using an algorithm designed to detect MARs (Singh et al., Nucleic *Acids Res.* 25:1419–25(1997))(FIG. 2b). The second putative MAR was identified by searching for a bipartite sequence which identifies MAR elements (van Drunen et al., *Nucleic Acids Res.* 27:2924–30 (1999)). The 14.5 kb EASE does not contain sequence elements, such as clusters of A and T boxes or topoisomerase II sites initially associated with MAR and SAR (Phi-Van et al., supra; Gasser et al., supra.) MAR sequences bind nuclear matrix proteins, are important for chromatin structure and may have a role in regulation of gene expression (reviewed by Davie, J. R., *J Cell. Biochem* 62:149–157 (1996)). The putative MAR region alone, however, does not have EASE activity. At least one plasmid containing high EASE activity PG5.7ΔS, does not include the putative MAR. The III box region also has high activity and partially co-localizes with the putative MAR as defined by Singh et al.

Expression vectors containing this 14.5 kb region and shorter fragments thereof were able to transform DXB11 CHO cells to high levels of expression of recombinant proteins at a frequency of >50%. The inventive EASE may improve expression of a recombinant protein driven by a promoter/enhancer region to which it is linked. Mapping studies indicated that >60% of the EASE activity is located in a 1.8 kb region of the DNA, from nucleotide 8671 to nucleotide 10516 of SEQ ID NO:1. In addition, a sequence nucleotide 8671 to nucleotide 9276 of SEQ ID NO:1 (the 604 bp EcoR1 to Hpa1 fragment) appears to be important for activity, as expression enhancement is eliminated if this region is deleted from PS.2SE1.8 (FIG. 1).

Figure 4:
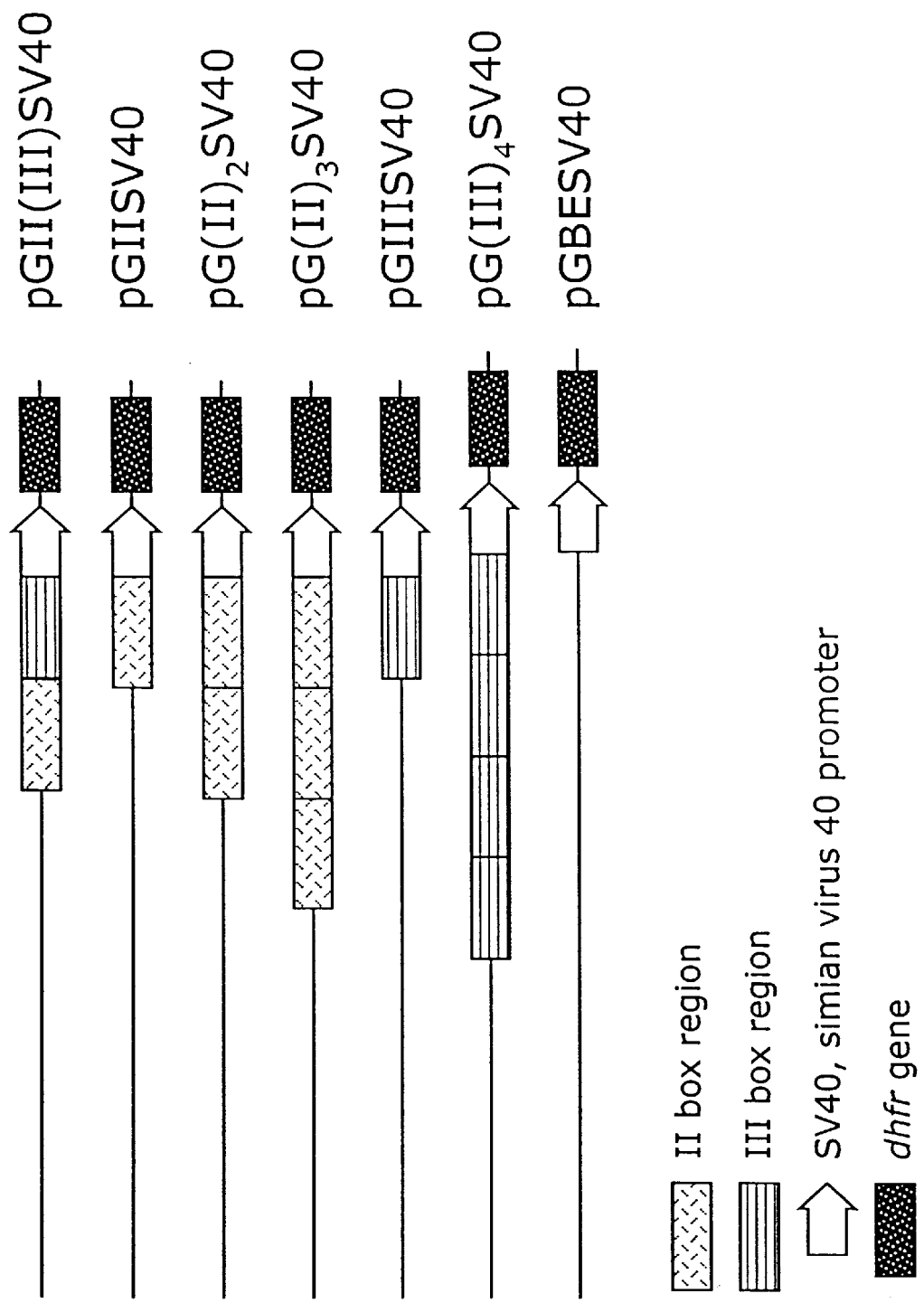
FIG. 4. Plasmids used for the colony forming assay. The II box region includes nucleotides 9991 to 11,257 from the EASE sequence as numbered in GenBank sequence AF193761. The III box region includes nucleotides 11,258 to 12,147 from the EASE sequence as numbered in Gen-Bank sequence AF93761. SV40 includes the enhancer and origin of replication Simian virus 40 DNA. dhfr gene is the cDNA encoding murine dihydrofolate reductase.

A 2.1 kb subdomain was found to contain EASE activity (Aldrich et al., *Cytotechnology* 28:9–17 (1998). More particularly, a 0.887 kb fragment of the 14.5 kb of CHO genomic DNA has been identified that demonstrates a high level of EASE activity either as a single element or in tandem arrays. (See Table 7 in Example 13 and pGIII SV40 and pG(III)$_4$ SV40 in FIG. 4.) The EASE activity of this region, which includes the III box, was measured by colony formation and/or cell growth in methotrexate (MTX) by cells transfected with plasmids pGIIISV40 and pG(III)$_4$SV40 (Table 7).

Even more particularly, it has been shown in the colony forming assay that a plasmid containing three copies of 0.628 nt III box has a similar level of EASE activity compared with the plasmid pG(III)$_4$SV40 and pGIIISV40 (Example 14).

Additional EASE sequences from the box III region have shown positive results in the colony forming assay. Specifically, polynucleotides comprising nucleic acid sequences selected from the group consisting of nucleotides 11538–12165, 11538–11692, 11538–11760, 11673–12165 (EASE3), 11813–12165 and 11899–12165, all of a nucleotide sequence as set forth in SEQ ID NO:1. And in particular, ligated forms of nucleotides 11538–11692 and 11813–12165 (EASE45) of SEQ ID NO:1, as well as 11538–11760 and 11899–12165 (EASE12) of SEQ ID NO:1.

Moreover, additional fragments of the 14.5 kb of CHO genomic DNA exhibiting EASE activity can be identified as described herein, as can similar EASE motifs from other types of cells or from other integration sites in transformed cells. Other combinations of the fragments described herein can also be developed, for example, sequences that included multiple copies of the EASE disclosed herein, or sequences derived by combining the disclosed EASE with other nucleotide sequences to achieve optimal combinations of regulatory elements. Regulatory elements can also be arranged to provide optimal spacing of the EASE from other regulatory regions. Similarly, the orientation of an EASE in a vector can be optimized to provide high levels of protein expression.

The EASE disclosed herein was isolated from Chinese hamster ovary (CHO) cells. Homologous expression augmenting elements are expected to exist in cells from other mammalian species as well as in cell lines derived from other tissue types, and can be isolated by techniques that are well-known in the art, for example by cross-species hybridization or PCR-based techniques. In addition, changes can be made in the nucleotide sequence set forth in SEQ ID NO:1 by site-directed or random mutagenesis techniques that are known in the art. The resulting EASE variants can then be tested for EASE activity as described herein. DNAs that are at least about 80% identical, more preferably at least about 90% identical, in nucleotide sequence to SEQ ID NO:1 or fragments thereof having EASE activity, for example the fragments identified herein as having EASE activity, are isolatable by routine experimentation, and expected to have EASE activity. For fragments of EASE, percent identity refers to that portion of the reference native sequence that is found in the EASE fragment. Accordingly, homologs of EASE and variants of EASE are also encompassed by the invention.

The expression of recombinant proteins is driven by an appropriate eukaryotic promoter/enhancer and the inventive EASE. Cells are transfected with a plasmid selected under low stringency for the dominant selectable marker and then selected again in higher stringency, for example, by using methotrexate, an inhibitor of DHFR in the selection media. The first selection yields positive transformants (i.e., DHFR$^+$ transformants in the case of methotrexate selection), and the second selection yields transformants that express high levels of the gene of interest.

Inclusion of an IRES sequence into vectors containing an EASE may be beneficial for enhancing expression of some proteins. The IRES sequence appears to stabilize expression of the gene of interest under high selective pressure (Kaufman et al. 1991, supra). For proteins that are processed well by the cells, the IRES sequence is not necessary to achieve high expression levels.

Cell populations expressing high levels of recombinant protein can be developed in five to seven weeks using a two step selection protocol as described herein. The absolute level of high expression will vary with the specific protein, depending on how well the protein is processed by the cell. We have observed stable cell pools expressing at least about 0.2 $\mu$g/10$^6$ cells/day, and in many cases greater than about 12 $\mu$g/10$^6$ cells/day, using a variety of cytokines and cytokine receptors. The time required to achieve this level of protein expression was almost half that observed for similar transformations done using vectors without EASE. With an additional cloning step, it is possible to develop cell lines expressing greater than about 24 $\mu$g/10$^6$ cells/day.

Transfection experiments demonstrate that EASE found in these DNA sequences have some characteristics of previously described cis-acting elements but do not fall into previously described definitions. Similar to LCR, MAR and SAR sequences, EASE activity is not detected in transient assays. Unlike these sequences however, EASE does not have A or T box clusters or topoisomerase, 2 sites typically found in these elements (Klehr et al., supra). A putative MAR element was identified using the algorithm of Shingh et al., but was not found to have EASE activity. Since EASE activity is not detected in transient assays, they also appear to be distinct from promoter and enhancer elements, which are detected with these methods.

EXPRESSION OF RECOMBINANT PROTEINS

Recombinant expression vectors include synthetic or cDNA-derived DNA fragments encoding the protein, operably linked to suitable transcriptional or translational regulatory elements derived from mammalian, viral or insect genes. Such regulatory elements include a transcriptional promoter, a sequence encoding suitable mRNA ribosomal binding sites, and sequences which control the termination of transcription and translation, as described in detail below. Mammalian expression vectors may also comprise nontranscribed elements such as an origin of replication, a suitable promoter and enhancer linked to the gene to be expressed, other 5' or 3' flanking nontranscribed sequences, 5' or 3' nontranslated sequences such as necessary ribosome binding sites, a polyadenylation site, splice donor and acceptor sites, and transcriptional termination sequences. An origin of replication that confers the ability to replicate in a host, and a selectable gene to facilitate recognition of transformants, may also be incorporated.

DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. Viral genomic promoters, control and/or signal sequences may be utilized to drive expression, provided such control sequences are compatible with the host cell chosen. Exemplary vectors can be constructed as disclosed by Okayama and Berg (*Mol. Cell. Biol.* 3:280, 1983). Non-viral cellular promoters can also be used (i.e., the β-globin and the EF-1α promoters), depending on the cell type in which the recombinant protein is to be expressed.

DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the BglI site located in the viral origin of replication is included.

Bicistronic expression vectors used for the expression of multiple transcripts have been described previously (Kim S. K. and Wold B. J., *Cell* 42:129, 1985; Kaufman et al. 1991, supra). pCAVDHFR is a derivative of pCD302 (Mosley et al Cell 1989) containing the coding sequence for mouse DHFR (Subramani et al., *Mol. Cell. Biol.* 1:854, 1981). The pCDE vector is a derivative of pCAVDHFR containing the murine encephalomyocarditis virus internal ribosomal entry site (nucleotides 260 through 824; Jang and Wimmer, *Genes and Dev.* 4:1560, 1990) cloned between the adenovirus tripartite leader and the DHFR cDNA coding sequence. Other types of expression vectors will also be useful in combination with the inventive EASE, for example, those described in U.S. Pat. No. 4,634,665 (Axel et al.) and U.S. Pat. No. 4,656,134 (Ringold et al.). The invention also contemplates the use of tricistronic, quattrocistronic, and higher order cistronic expression vectors.

HOST CELLS

Transformed host cells are cells which have been transformed or transfected with expression vectors constructed using recombinant DNA techniques and which contain sequences encoding recombinant proteins. Expressed proteins will preferably be secreted into the culture supernatant, depending on the DNA selected, but may be deposited in the cell membrane. Various mammalian cell culture systems can be employed to express recombinant protein. Examples of suitable mammalian host cell lines include the COS-7 lines of monkey kidney cells, described by Gluzman (*Cell* 23:175, 1981), and other cell lines capable of expressing an appropriate vector including, for example, CV-1/EBNA (ATCC CRL 10478), L cells, C127, 3T3, Chinese hamster ovary (CHO), HeLa and BHK cell lines.

A commonly used cell line is DHFR$^-$ CHO cells which are auxotrophic for glycine, thymidine and hypoxanthine, and can be transformed to the DHFR$^+$ phenotype using DHFR cDNA as an amplifiable dominant marker. One such DHFR$^-$ CHO cell line, DXB11, was described by Urlaub and Chasin (*Proc. Natl. Acad. Sci. USA* 77:4216, 1980). Other cell lines developed for specific selection or amplification schemes will also be useful with the inventive EASE.

PREPARATION OF TRANSFORMED MAMMALIAN CELLS

Several transformation protocols are known in the art, and are reviewed in Kaufman, R. J., *Meth. Enzymology* 185:537 (1988). The transformation protocol chosen will depend on the host cell type and the nature of the gene of interest, and can be chosen based upon routine experimentation. The basic requirements of any such protocol are first to introduce DNA encoding the protein of interest into a suitable host cell, and then to identify and isolate host cells which have incorporated the heterologous DNA in a stable, expressible manner.

One commonly used method of introducing heterologous DNA is calcium phosphate precipitation, for example, as described by Wigler et al. (*Proc. Natl. Acad. Sci. USA* 77:3567, 1980). DNA introduced into a host cell by this method frequently undergoes rearrangement, making this procedure useful for cotransfection of independent genes.

Polyethylene-induced fusion of bacterial protoplasts with mammalian cells (Schaffner et al., *Proc. Natl. Acad. Sci. USA* 77:2163, 1980) is another useful method of introducing heterologous DNA. Protoplast fusion protocols frequently yield multiple copies of the plasmid DNA integrated into the mammalian host cell genome; however, this technique requires the selection and amplification marker to be on the same plasmid as the gene of interest.

Electroporation can also be used to introduce DNA directly into the cytoplasm of a host cell, for example, as described by Potter et al. (*Proc. Natl. Acad. Sci. USA* 81:7161, 1988) or Shigekawa and Dower (*BioTechniques* 6:742, 1988). Unlike protoplast fusion, electroporation does not require the selection marker and the gene of interest to be on the same plasmid.

More recently, several reagents useful for introducing heterologous DNA into a mammalian cell have been described. These include Lipofectin® Reagent and Lipofectamine™ Reagent (Gibco BRL, Gaithersburg, Md.). Both of these reagents are commercially available reagents used to form lipid-nucleic acid complexes (or liposomes) which, when applied to cultured cells, facilitate uptake of the nucleic acid into the cells.

A method of amplifying the gene of interest is also desirable for expression of the recombinant protein, and typically involves the use of a selection marker (reviewed in Kaufinan, R. J., supra). Resistance to cytotoxic drugs is the characteristic most frequently used as a selection marker, and can be the result of either a dominant trait (i.e., can be used independent of host cell type) or a recessive trait (i.e., useful in particular host cell types that are deficient in whatever activity is being selected for). Several amplifiable markers are suitable for use in the inventive expression vectors (for example, as described in Maniatis, *Molecular Biology: A Laboratory Manual*, Cold Spring Harbor Laboratory, NY, 1989; pgs 16.9–16.14).

Useful selectable markers for gene amplification in drug-resistant mammalian cells are shown in Table 1 of Kaufman, R. J., supra, and include DHFR-MTX resistance, P-glycoprotein and multiple drug resistance (MDR)-various lipophilic cytoxic agents (i.e., adriamycin, colchicine, vincristine), and adenosine deaminase (ADA)-Xyl-A or adenosine and 2'-deoxycoformycin.

Other dominant selectable markers include microbially derived antibiotic resistance genes, for example neomycin, kanamycin or hygromycin resistance. However, these selection markers have not been shown to be amplifiable (Kaufman, R. J., supra,). Several suitable selection systems exist for mammalian hosts (Maniatis supra, pgs 16.9–16.15. Co-transfection protocols employing two dominant selectable markers have also been described (Okayama and Berg, *Mol. Cell Biol* 5:1136, 1985).

A particularly useful selection and amplification scheme utilizes DHFR-MTX resistance. MTX is an inhibitor of DHFR that has been shown to cause amplification of endogenous DHFR genes (Alt F. W., et al., *Journal of Biological Chemistry* 253:1357, 1978) and transfected DHFR sequences (Wigler M., et al., *Proc. Natl. Acad. Sci. USA* 77:3567, 1980). Cells are transformed with DNA containing the gene of interest in one expression cassette, linked or unlinked to the DHFR gene in a second expression cassette. The two genes can also be in one bicistronic expression unit (Kaufman et al., 1991 supra and Kaufman R. J., et al., *EMBO J* 6:187, 1987). Transformed cells are grown in media containing successively greater amounts of MTX, resulting in greater expression of the DHFR gene, as well as the gene of interest.

Useful regulatory elements, described previously, can also be included in the plasmids used to transform mammalian cells. The transformation protocol chosen, and the elements selected for use therein, will depend on the type of host cell used. Those of skill in the art are aware of numerous different protocol and host cells, and can select an appropriate system for expression of a desired protein, based on the requirements of their cell culture systems.

The relevant disclosures of all references cited herein are specifically incorporated by reference. The following examples are intended to illustrate particular embodiments, and not limit the scope, of the invention.

EXAMPLES

Example 1

Genomic Library Screening and Subcloning

A transformed CHO cell line (designated the 2A5-3 cell line) expressing high levels of an immunoglobulin Fc fusion protein comprising the extra cellular domain of the 80 Kd receptor for Tumor Necrosis Factor (TNFrFc; Mohler et al., *J. Immunol.* 151:1548, 1993; U.S. Pat. No. 5,395,760, issued Mar. 7, 1995; the disclosure of both of which are incorporated by reference) was selected for preparation of a genomic library since Southern blot analysis indicated that the high expression of TNFrFc expression observed for this cell line is driven by a single integration of an expression cassette encoding TNFrFc. DNA was isolated from these cells, partially digested with MboI and cloned into a lambda FIX II cloning vector (Stratagene custom genomic library; Stratagene La Jolla, Calif.) to form a library. The p80 TNF receptor coding sequence, along with 14.4 kb of cellular flanking sequences, was cloned from the library as described below.

To screen the library; approximately $2\times10^4$ plaque forming units (pfu) were allowed to form per 250 cm plate. Plaques were transferred to nitrocellulose membranes (Schleicher and Schuell, Keene, N.H.) and lysed using standard protocols supplied by Stratagene. The filters were probed with random primed NotI PvuII DNA fragment encoding a cell surface portion of p80 TNF receptor extracellular domain (Mohler et al. supra). Hybridizations were performed at 63° C. in hybridization buffer [(10×Denharts solution (Maniatis supra, pg. 9.49), 0.05M Tris pH 7.5, 1M NaCl, 0.1% sodium pyrophosphate, 1% SDS, 4 µg/ml salmon sperm DNA]. Filters were washed as follows: initial wash in 0.1% SDS, 0.1% SSC (Maniatis supra, B.13) at 42° C. for 30 min., followed by two additional washes in the same solution for 60 min. at 63° C. The final two washes were at 63° C. for 60 min. using 0.1% SDS and 0.01% SSC. A single positive recombinant clone was identified after screening about $4\times10^5$ recombinants. This clone, which was designated 2A5-3 λ, was used in all subsequent analyses. The nucleotide sequence of the CHO genomic DNA from this clone is shown in SEQ ID NO:1. The 2A5-3 λ was deposited with the American Type Culture Collection, Rockville Md., under the terms of the Budapest Treaty on Jan. 4, 1996, and given accession number 97411.

Example 2

Tissue Culture

Dihydrofolate reductase (DHFR) deficient Chinese hamster ovary (CHO) cells DXB11 (Chasin and Urlaub, supra) cells were maintained in Dulbecco's minimal essential medium and F12 (DMEM:F12) supplemented with 7.5% fetal bovine serum (FBS; Hyclone, Logan, Utah; or Sigma, St. Louis, Mo.), 2 mM L-glutamine, 90 µM thymidine (T), 90 µM hypoxanthine (H) and 120 µM glycine (G). For DHFR selection studies and methotrexate selections, cells were cultured in DMEM:F12 lacking GHT and supplemented with 7.5% dialyzed FBS, 6 mM L-glutamine and 1 mM asparagine. For methotrexate selections, methotrexate (MTX; Lederle Laboratories, Pearl River, N.Y.) was added to the selection media at appropriate concentrations. When neomycin selection was employed, 400 µg/ml of G418 (Gibco, Grand Island, N.Y.) was added to the media. The cells were transfected using calcium phosphate transfection (Wigler et al. supra), or Lipofectamine™ transfection as recommended by the supplier (Gibco BRL, Gaithersburg, Md.).

Example 3

Enzyme Linked Immunosorbent Assays (ELISA)

Production of recombinant proteins can be monitored by any assay suitable for detecting the desired protein, including binding assays, inhibition assays, and biological assays. A particularly useful assay is the antibody sandwich enzyme-linked immunosorbent assay (ELISA), which is well known in the art (for example, adaptations of the techniques disclosed in Engvall et al., *Immunochem.* 8:871, 1971 and in U.S. Pat. No. 4,703,004). In this assay, a first antibody specific for a protein of interest (usually a monoclonal antibody) is immobilized on a substrate (most often, a 96-well microtiter plate), then a sample containing the protein is added and incubated. A series of dilutions of a known concentration of the protein is also added and incubated, to yield a standard curve. After a wash step to remove unbound proteins and other materials, a second antibody to the protein is added. The second antibody is directed against a different epitope of the protein, and may be either a monoclonal antibody or a polyclonal antibody.

A conjugate reagent comprising an antibody that binds to the second antibody conjugated to an enzyme such as horse radish peroxidase (HRP) is added, either after a second wash step to remove unbound protein, or at the same time the second antibody is added. Following a suitable incubation period, unbound conjugate reagent is removed by washing, and a developing solution containing the substrate for the enzyme conjugate is added to the plate, causing color to develop. The optical density readings at the correct wavelength give numerical values for each well. The values for the sample are compared with the standard curve values, permitting levels of the desired protein to be quantitated.

To quantitate trimeric CD40 ligand, a CD40L ELISA using two monoclonal antibodies (MAb) was developed. One antibody was directed against an oligomerizing zipper domain present in the trimeric protein, and the second antibody was directed against the human CD40 ligand portion of the molecule. The first MAb was adsorbed onto plates overnight, and the peroxidase (HRP) conjugated second antibody was added after a wash step. In several experiments quantities of between 0.78 and 50 ng/ml CD40L were detected.

A similar ELISA was used to quantitate recombinant human tumor necrosis factor receptor fusion protein (TNFrFc). In this ELISA two monoclonal antibodies against different epitopes of TNFrFc were used. Again, the first MAb was adsorbed onto plates overnight, and the peroxidase (HRP) conjugated second antibody was added after a wash step. In several experiments quantities of between 0.78 and 50 ng/ml TNFrFc were detected.

For detecting recombinant Flt-3 ligand (Flt-3L), a somewhat different ELISA was used, employing a monoclonal antibody and a rabbit polyclonal antiserum. As described previously, the MAb was adsorbed onto plates overnight. A solution containing both the polyclonal anti-Flt-3L and the peroxidase (HRP)-conjugated second antibody (donkey anti-rabbit immunoglobulin) was added after the first wash step to remove unbound proteins. In several experiments quantities of between 1.56 and 100 ng/ml Flt-3L were detected.

Example 4

Sequencing and Data Base Searches

DNA was sequenced using shotgun sequencing as described previously (Bankier, *Meth. Mol. Biol.*23:47, 1993) or primer walking using the ABI Taq DyeDeoxy Terminator Cycle Sequencing kit on an automated DNA sequencer (model 373a; Applied Biosystems, Foster City, Calif.). The 2A5-3 λ DNA was characterized by performing several different type of computer analysis.
(a) Compositional Analysis The 2A5-3 λ sequence was scanned for regions of high A+T content using a combination of the three computer programs available from the Wisconsin Package from the Genetics Computer Group (Program Manual for the Wisconsin Package, Version 8, September 1994, Genetics Computer Group, 575 Science Drive, Madison, Wis., USA 53711), namely SIMPLIFY, WINDOW, and STATPLOT. To search for regions of high A+T content, a sliding window of 50 base pairs was slid across the 2A5-3 λ sequence in one base-pair increments, and the percentage A+T within that window was plotted. Areas of interest were those where the average A+T content was consistently above 70 percent. One region with >200 base pairs with >70% A+T content was found between the two SwaI sites (nucleotides 10517 through 12591 of SEQ ID NO: 1).
(b) Transcription Enhancement Motifs A search was performed for three known transcription-enhancing motifs using the GCG program MOTIFS: "Topo-II" [GTNWAYATTNATNNR], "T-box" [ATATTT/AATATT], and "A-box" [AATAAAYAAA] (Klehr et al. supra). This program scans a query sequence in a linear fashion looking for an exact match to each specified input motif. For each motif, degeneracies were designated with symbols using the naming conventions of the International Union of Biochemistry (IUB). No "topo-II boxes" were found in the 14.5 kb of CHO DNA in the 2A5-3 λ DNA. Two "A-boxes" and 26 "T-boxes" were found dispersed through out this region of CHO DNA. The "A boxes" and "T-boxes" were not clustered as typical for MAR and SAR regions.

The EASE sequence was also searched for putative matrix attachment sites (MARs) using a sequence analysis program designed to find matrix attachment regions (Singh et al., *Nucleic Acids Res.* 25:1419–25(1997)). This program detected one putative MAR (FIG. 2). A second putative MAR was found in the 5' end of 14.5 kb EASE DNA by searching for a bipartite sequence described by van Drunen et al. (*Nucleic Acids Res.* 27:2924–30 (1999)).
(c) Sequence Database Search for Similarity Database searches of the GenBank DNA sequence databases and the SwissProt and PIR protein sequence databases were performed using the BLAST algorithm of Altschul et al. (*J. Mol. Biol.* 215:403; 1990). This algorithm is optimized for finding segments of local similarity without inserting gaps in the alignment. BLAST searches on both the CHO insert of the 2A5-3 λ DNA sequence and a dynamic protein translation in all six reading frames failed to produce significant matches with any known transcriptional activation sequences.
(d) Coding Sequence Analysis The computer program GRAIL (Uberbacher, E. C., and Mural, R. J., *Proc. Natl. Acad. Sci. USA* 88:11261; 1991), a neural-network based gene-recognition system was used to scan the 2A5-3 λ sequence for potential coding regions. A GRAIL search evaluates the coding potential of a DNA sequence within a sliding 100 bp window. To avoid bias, searches for potential coding regions were performed both with and without respect to additional genomic features (e.g., splice junctions and translation starts). The results of GRAIL searches did not indicate any regions of high protein coding potential within the CHO insert of the 2A5-3 λ sequence.

Example 5

Expression of Proteins Using the Cloned Sequences

The purpose of this experiment was to determine if the sequences surrounding the TNFrFc integration site in CHO cell line 2A5-3 could confer high expression of this protein when randomly integrated into DXB11 cells. This integration site was cloned as described in Example 1, and DXB11 CHO cells were co-transfected with either 5 μg of 2A5-3 λ DNA or 5 μg of a control plasmid, and 1 μg of pSV3NEO (this expression vector contains the G418 resistance marker gene driven by the SV40 promoter) DNA using calcium phosphate transformation. Control cells were transformed with an expression vector for TNFrFc called pCAVDH-FRp80 consisting of the CMV promoter/enhancer driving expression of a bicistronic message where the first intron is sequence encoding TNFrFc and the second intron encodes murine DHFR. pCAVDHFRp80 is the plasmid that was used to construct the 2A5-3 cell line. After a 48 hr. recovery period cells were split 1:3 or 1:2 into 10 cm dishes in media containing 400 μg/ml G418. After a seven to nine day selection in G418-containing medium, resistant colonies were detected and 24 pools consisting of one to three colonies were selected and seeded into 24 well plates.

When the cells reached confluence, the medium was changed to medium lacking GHT to select for DHFR$^+$cells. Eight of the doubly selected pools were assayed for specific productivity of TNFrFc by ELISA as described in Example 4, and it was found that 40% of the pools had expression levels 75% or greater than that of the parental cell line (see Table 1 below).

TABLE 1

Specific Production of TNFrFc
by Cells Transformed with 2A5-3 λ DNA

| Cell line or pool* | μg/10$^6$ cells/day |
|---|---|
| 1. 2A5-3 | 2.88 |
| 2. 2A5-3.3 | 3.40 |
| 3. 2A5-3.6 | 1.45 |
| 4. 2A5-3.8 | 1.17 |
| 5. 2A5-3.10 | 0.04 |
| 6. 2A5-3.11 | 1.16 |
| 7. 2A5-3.13 | 1.99 |
| 8. 2A5-3.15 | 2.40 |
| 9. 2A5-3.24 | 4.00 |
| 10. p80.8 | BR** |
| 11. p80.9 | 0.01 |
| 12. p80.20 | 0.02 |

*1: parental cell line(positive control); 2–9: cell pools transformed with 2A5-3 λ 10–12: cell pools transformed with CAVDHFRTNFrp80 (negative control)
**BR: below range Three of these pools were monitored over 10 passages and it was found that expression remained greater than or equal to that of the parental cell line, as shown in the Table 2 below.

TABLE 2

Specific Production of TNFrFc by Cells
Transfected with 2A5-3 λ DNA, Multiple Passages

| Cells | passage # | μg/10$^6$ cells/day |
|---|---|---|
| 2A5-3 parental cell line | 75 | 1.59 |
|  | 83 | 1.30 |
| 2A5-3.8 pool | 3 | 2.75 |
|  | 11 | 1.46 |
| 2A5-3.13 pool | 3 | 2.55 |
|  | 11 | 1.91 |
| 2A5-3.15 pool | 3 | 4.17 |
|  | 11 | 2.65 |

This experiment was repeated by doing a second co-transfection, and similar results were obtained. In both co-transfection experiments, a decrease in specific production as the pools were passaged was observed, most likely due to the fact that, in the mixed cell population of the pools, faster growing cells that produced lower amounts of recombinant protein outgrew the slower growing, higher producing cells. Even with the decrease in specific production, all cell pools maintained production levels greater than that or equal to that of the parental cell line. The results indicated that the 2A5-3 λ DNA insert can confer expression of an indicator protein near that of the parental cell line at a high frequency (≧40%) when randomly integrated into DXB11 CHO cell DNA.

Example 6

Identification of Fragments Having EASE Activity

In a second series of co-transfection experiments, it was determined that shorter segments of 2A5-3 λ DNA could confer high expression of recombinant proteins, but with lower frequency than 2A5-3 λ. Various portions of the phage insert were subcloned into bluescriptII (Strategene, La Jolla, Calif.), or pGEM-11Zf(−) (Promega, Madison, Wis.) for sequencing and restriction mapping, using standard techniques of restriction enzyme cutting and ligation (see FIG. 1). For protein expression studies, various inserts were derived from the phage clone shown in FIG. 1A, and subcloned into pGEM1 (Promega, Madison, Wis.). Restriction sites used for subcloning are indicated in the restriction map presented in FIG. 1A.

DXB11CHO cells were transfected with 0.2 μg TNFrFc encoding sequences for each TNFrFc expression plasmid and 0.1 μg of pSV3neo using the Lipofectamine™ reagent (Gibco BRL, Gaithersburg, Md.). After a 48 hour period, the cells were split 1:4 or 1:40 into G418 selective media. Colonies were visible in a 7–10 day time period, at which point the media was changed to −H or −GHT DHFR selective media. After selection for 10–13 days in DHFR selective media, pools of 1–3 colonies were picked and plated in 24 well vessels. The cultures were sampled at confluence and frequency of high expression was scored (see Table 3). It was found that high expression could be achieved with vectors containing at a minimum an EcoR1 to SwaI 2.8 kb fragment 3.9 kb from the CMV promoter and a 1.9 kb sequence immediately 5' of the CMV promoter (PG5.7ΔS). Plasmids containing larger amounts of insert (PG8.5 and PG5.7) were also effective at enhancing expression.

TABLE 3

Percent of Pools Expressing >0.5 μg/ml Recombinant Protein

| | Recombinant Protein: | | | |
|---|---|---|---|---|
| | HuTNRrFc | | HuFlt-3L | |
| Construct: | exp't 1 | exp't 2 | exp't 1 | exp't 2 |
| 2A5-3 λ | 100 (n = 8) | 100 (n = 6) | na | na |
| PG8.5 | 70 (n = 19) | 100 (n = 11) | na | na |
| PG5.7 | 40 (n = 14) | 100 (n = 13) | 100 (n = 12) | 80 (n = 12) |
| PG5.7ΔS | 100 (n = 12) | 50 (n = 10) | na | 50 (n = 6) |
| PG.2SE1.8 | na$^1$ | 100 (n = 12) | na | na |
| PG.2SH1.2 | na | 0.0 (n = 12) | na | na |
| PG.2.2 | 0 (n = 12) | 0.0 (n = 12) | na | 0.0 (n = 12) |
| PG.2 | na | 0.0 (n = 12) | na | na |

1: not assayed

A similar set of expression plasmids comprising DNA encoding the extracellular portion of Flt-3 ligand (Lyman et al., *Blood* 83:2795, 1994 and U.S. Ser. No. 08/242,545, filed May 11, 1994) was prepared and tested as described above. As was observed for TNFrFc, high levels of expression could be achieved with the PG5.7ΔS vector but not the PG2.2 vector or the PG.2 vector. The results of these experiments indicated that the high frequency of high recombinant protein expression is not protein specific and that the 1.8 kb EcoR1 to Swa1 band is a region of high EASE activity.

Example 7

Comparison of Specific Productivity

To more accurately quantitate the expression from clones transfected with plasmids containing shorter lengths of integration site DNA and compare it to clones derived from transfection with the phage DNA, the specific productivity of the three highest expressing pools transformed with the PG5.7ΔSTNFrFc construct and the three highest expressing pools transformed with the phage DNA were compared (Table 4). In this experiment it was found that the expression level for all six pools was not significantly different when compared using a standard T test (p=0.14).

TABLE 4

Comparative expression of recombinant protein expressed using Phage DNA or PG5.7ΔS

| Cell pool | Average μg/10$^6$ cells/day[1] |
|---|---|
| 2a5.3.3 | 3.06 ± 0.60 |
| 2a5.3.7 | 2.67 ± 0.28 |
| 2a5.3.11 | 3.37 ± 0.54 |
| PG5.7ΔS.1 | 2.25 ± 0.35 |
| PG5.7ΔS.4 | 2.79 ± 0.89 |
| PG5.7ΔS.6 | 2.65 ± 0.34 |

1: n = 2

These results, taken together with the frequency data shown in Table 3, indicates that the PG5.7ΔS vector contains all the sequence information necessary for high level expression.

Example 8

Characterization of the EASE

To further characterize the expression enhancing activity found in the 2A5-3 λ-derived expression vectors, a colony forming assay was performed. Here, 1.6 μg DHFR encoding sequences from plasmids PG8.5, PG5.7ΔS, PG.2SE1.8, PG.2SH1.2 and PG.2 were transfected into DXB11 cells using Lipofectamine™. After a 48 hour expression period cells were plated at 1×10$^4$ cells/plate in –GHT medium containing various concentrations of MTX. After nine to eleven days, the plates were fixed with methanol and stained with methylene blue for colony formation. Greater colony formation was detected with plasmids PG8.5, PG5.7ΔS, and PG.2SE1.8 compared with plasmids PG.2SH1.2 and PG.2 plasmid at 0 nM and 10 nM MTX (See Table 5).

TABLE 5A

Colony formation using pGEM vectors

| | Colonies/nM Methotrexate | | | |
|---|---|---|---|---|
| Plasmid: | 0 nM | 10 nM | 25 nM | 50 nM |
| PG8.5 | 206 | 65 | 8 | 3 |
| PG5.7ΔS | 224 | 57 | 6 | 3 |

TABLE 5A-continued

Colony formation using pGEM vectors

| | Colonies/nM Methotrexate | | | |
|---|---|---|---|---|
| Plasmid: | 0 nM | 10 nM | 25 nM | 50 nM |
| PG.2SE1.8 | 168 | 28 | 0 | 2 |
| PG.2SH1.2 | 51 | 2 | 0 | 1 |
| PG.2 | 85 | 22 | 1 | 0 |

These data indicate that the 1.8 kb EcoR1 to Swa1 fragment contained in PG.2E1.8 is a region of high EASE activity. Moreover the 0.6 kb Hpa1 to EcoR1 fragment is important for EASE activity as deletion of this region results in loss of EASE activity (compare results with PG.2SH1.2 and PG.2). Plasmids with longer lengths of CHO genomic DNA, i.e., PG8.5 and PG5.7ΔS, gave greater colony formation at increased selective pressure (25 nM and 50 nM MTX) when compared with plasmid PG.2SE1.8. This differential colony formation at higher selective pressure indicates that the presence of longer stretches of CHO genomic DNA in a plasmid confers higher frequency of high expression than shorter stretches of CHO genomic DNA.

In a related series of studies, the relative colony formation of the following box III EASE sequences were tested: nucleotides 11538 through 12165 of SEQ ID NO:1, EASE45, EASE12 and EASE3. The colony forming assay described above was used, except for the following modifications. the DNA was linearized with PvuI using standard techniques and 10 μg of linearized DNA was transfected into DXB 11 cells using electroporation. After a 48 hour expression period, cells were plated at 1×10$^5$ and 1×10$^6$ cells/plate in –GHT medium containing various concentrations of MTX. After nine to eleven days, the plates were fixed with methanol and stained with methylene blue for colony formation.

TABLE 5B

Colony Formation Assay

| | Nucleotides of SEQ ID NO: 1 | Relative Colony Formation | |
|---|---|---|---|
| Fragment | | Exp. 1 | Exp. 2 |
| Box III | 11538–12165 | 1 | 1 |
| EASE45 | 11538–11692 ligated to 11813–12165 | 0.3 | 0.73 |
| EASE12 | 11538–11760 ligated to 11899–12165 | 0.5 | 1.1 |
| EASE3 | 11673–12165 | 0.5 | 1.2 |

This data indicates that EASE12 and EASE3 have an additional amplifying effect on colony formation relative to the Box III fragment.

Example 9

Transient Expression Assays

Transient expression assays were done to determine if the expression augmenting activity is acting like a classical enhancer or promoter, which can increase expression in transiently expressed non-chromosomal DNA. Plasmid PG8.5 and plasmid PG2.2, the former of which had been shown to have EASE activity, while the latter did not (as demonstrated in Example 6), were transiently transfected into CHO cells using a Lipofectamine™ technique as described previously. After 48 hrs. supernatants were collected and tested for TNFrFc expression using ELISA as previously described. In contrast to the stable expression experiment in Example 6, these two plasmids gave the same level of expression of recombinant TNFrFc in the transient expression assay (see Table 6).

TABLE 6

Transient expression of TNFrFc

| Plasmid | Average TNFrFc (ng/ml[1]) |
|---|---|
| PG2.2 | 95.75 ± 41.97 |
| PG8.5 | 105.5 ± 26.02 |

1: n = 4

These data indicate that EASE function requires chromosomal integration unlike previously known enhancers and/or promoters.

Example 10

Reduction in Time Required for Protein Production

Flt-3L was expressed in CHO cells using three different expression vectors, pCDE (see "expression of recombinant proteins"), PG5.7 and PG5.7I. The vector PG5.7I is a derivative of PG5.7 which contains the murine encephalomyocarditis virus IRES cloned between the adenovirus tripartite leader and the DHFR cDNA of PG5.7. DXB11 CHO cells were transfected with the three Flt-3L expression plasmids described above using the Lipofectamine™ method and selected for DHFR expression in –GHT media. DHFR$^+$ colonies were then pooled and plated in 0 nM, 25 nM, 50 nM and 100 nM MTX and allowed to grow to confluence, at which time specific productivities of pools transfected with each construct was determined. The expression from each construct was similar at each MTX level, however the time required for completing the analysis was only four to five weeks for the cell pools made with the PG5.7I vector compared with seven to eight weeks required for the pCDE and PG5.7 vectors.

This trend (obtaining similar expression levels in shorter periods of time when EASE is present) has been observed with at least six different proteins, three expressed in the pCDE vector and three expressed with the PG5.7I vector. In general, it takes two to five weeks less time to produce recombinant protein using expression vectors containing EASE and IRES sequences compared with similar expression vectors containing the IRES sequence alone.

Example 11

Use of EASE in Production-scale Expression

Recombinant HuCD40L was expressed in CHO cells for manufacturing using the PG5.7I vector. Here DNA encoding a trimeric form of huCD40L was cloned into the PG5.7I vector and DNA from the resulting CD40L expression plasmid was transfected into CHO cells using Lipofectamine™. Cells were first selected for the DHFR$^+$ phenotype, then pooled and selected in 50 nM MTX. Cells which grew in 50 nM MTX were cloned using a soft agar cloning method (Gibson et al., *BioTechniques* 15:594, 1993). Eighteen colonies were picked and screened for specific productivity of huCD40L and two cell lines were selected for suspension adaptation and production runs in fed batch bioreactor runs. During two production runs of 10 and 8 days each using one of the cell lines (the 50-B4 line), cells maintained an average specific productivity of approximately 24 and 25 μg/10$^6$ cells/day respectively. The final titers were 1.02 and 1.09 g/L by ELISA, for the 10 day and 8 day runs respectively. This example demonstrates that use of this vector in manufacturing development represents an improvement in the art since high levels of recombinant protein expression were achieved in a scalable format with a minimum of screening (18 cell lines screened) and selection steps (two steps).

Example 12

Plasmid Constructions

Figure 3:
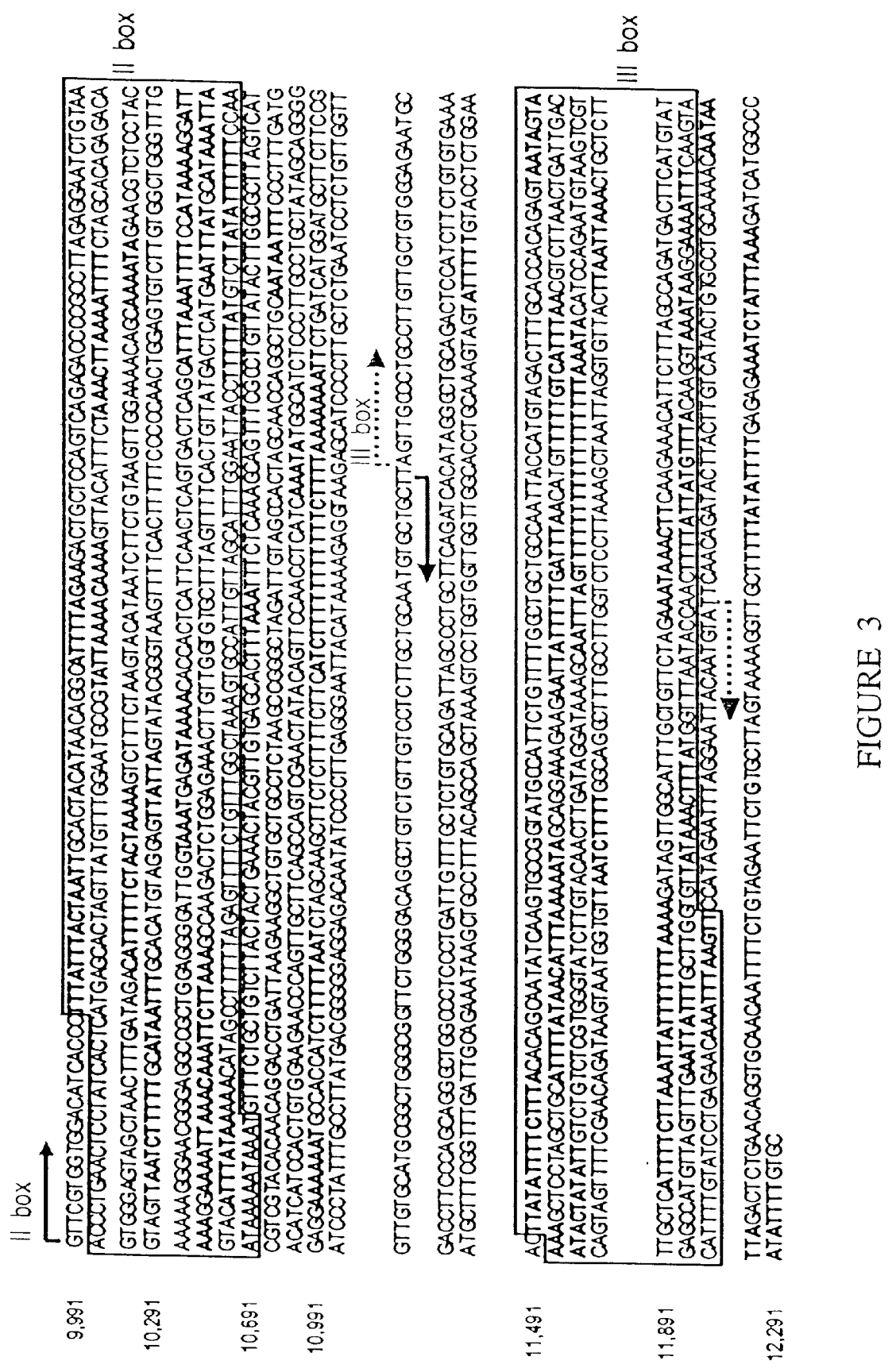

Plasmid pG.2B (Aldrich et al., *Cytotechnology* 28:9–17 (1998)) was used as the base for plasmids pG(III)$_4$SV40 and pG3.8SV40. The human cytomegalovirus promoter was removed by digestion with BamHI (New England Biolabs) and KpnI (New England Biolabs), the ends filled using Pfu polymerase (Stratagene) and an EcoRI (New England Biolabs) linker inserted. This plasmid was named pG.2BE. Plasmid pGBESV40 was constructed by cloning the SV40 promoter, which was amplified by PCR, behind the EcoRI site of pG.2BE. EASE II and III box containing regions (FIG. 3) were amplified by PCR. Plasmids pGII, pG(II)$_2$ and pG(II)$_3$ were made by cloning one, two or three copies of the II box containing region between the BamHI and EcoRI sites of pGBESV40. Plasmids pGIIISV40 and pG(II1)$_4$SV40 were constructed by cloning either one or four copies of the III box containing region into pGBESV40. PG3.8SV40 was constructed by inserting a 3.8 BamHI fragment from 2A5-3λ up stream of the SV40 promoter in pGBESV40. The location of the BamHI fragment in 2A5-3λ is shown in FIG. 1B.

Example 13

Cell Culture

Colony forming assay—Plasmids were linearized with FspI restriction enzyme and transfected into DHFR- DXB-11 CHO cells (Urlaub et al., *Proc. Natl. Acad. Sci. USA* 77:4216–20 (1980)) by electroporation (*Cytotechnology* 28:9–17(1998). Following 72 hours of recovery in nonselective medium (DMEM:F12 supplemented with 7.5% bovine calf serum (Hyclone), 2 mM L-glutamine, 90 μM thymidine [T], 90 μM hypoxanthine [H] and 120 μM glycine [G]), 3×10$^5$ cells were seeded per T25 flask into –GHT medium (DMEM:F12 supplemented with 7.5% dialyzed fetal bovine scrum (Sigma), 6 mM L-glutamine, 1 mM asparagine) to select for DHFR expression. When the cultures became confluent, they were harvested and seeded at 1×10$^5$ cells per T75 flask in –GHT medium. After this passage, they were plated at a density of 2×10$^5$ cells per 10 cm dish in 75 nM MTX. Three weeks later, the plates were stained with methylene blue and the colonies counted.

In this assay, colony formation could result from either high transcription or amplification of the integrated DHFR, since colony formation would require a high DHFR level to overcome DHFR inhibition by MTX. As shown in Table 7, considerable variability was observed in the colony formation from pool to pool for each plasmid. The pools with either the III box or the multi III box showed increased frequency of colony formation when compared to the II box plasmids or the control vector that did not contain an EASE fragment.

TABLE 7

Colony formation of various EASE constructs

| Plasmids | Number of transfections | % transfections with colonies >100 |
|---|---|---|
| pGBESV40 | 5 | 20% |
| pGIISV40 | 6 | 33% |
| pG(II)$_2$SV40 | 6 | 17% |
| pG(II)$_3$SV40 | 4 | 0% |
| pGIIISV40 | 6 | 67% |
| pG(III)$_4$SV40 | 11 | 64% |

Amplification assay—The plasmids pG(III)$_4$SV40 and pG3.8SV40 were linearized with FspI restriction enzyme and electroporated into DXB-11 CHO cells. Subsequently, as with the colony forming assay, the cells were selected for two passages in −GHT selective medium, first at a seeding density of 3×10$^5$ cells per T75 flask followed by a seeding density of 1×10$^5$ cells per T75 flask and was plated in medium containing 75 nM MTX. The cell pools were selected twice in medium containing MTX. The first selection was done at a seeding density of 1×10$^6$ cells per T75 flask and the second at 5×10$^5$ cells per T75 flask.

As shown in Table 8, the selection in −GHT occurred at essentially the same rate for both constructs. A difference in growth rates was detected only during the first selection in media containing 75 nmMTX. This difference was indicated by the increased number of days to reach confluence and the number of pools that survived in 75 nmMTX. For the EASE containing plasmids, all pools survived in MTX and grew to confluence in less time compared with the control plasmids. Only three of the seven pools generated with the pG3.8SV40 plasmid grew in the presence of 75 nm MTX.

SV40, which is less than pGI.9SV40 which is equal to pGIIISV40 and pG(III)$_4$SV40. Plasmids with the highest EASE activity were >2.6 times more active than the control pGBESV40.

Example 15

Purification of CHO HMG Proteins and Electrophoretic Mobility Shift Assay (EMSA)

Crude HMG protein samples were obtained from DXB-11 CHO cells as described (Reeves et al., *J. Biol. Chem.* 265:8573–82 (1990); Reeves et al., *Meth. Enzymol.* 304:155–88 (1999)). Probes for the EMSA were synthesized by PCR using the Expand High Fidelity PCR System (Boehringer-Mannheim Biochemicals) with the following oligonucleotides: 5'-CATTCAACTCAGTGACTCA-3', 5'-AGTAAGACAGCAGAAACATT-3' (probe 1), 5'-ATGACGGGGGAGGAGAC-3', 5'-AGGACTTTAGCTGGCTGTA-3' (probe 2), 5'-GGCACCTGCAAAGTAGTA-3' and 5'-CAAGATACCCACGAGACA-3' (probe 3). The DNA probes were end labeled with [alpha$^{32}$P]ATP (Amersham) by T4 DNA polymerase (Sambrook et al., *Molecular Cloning: A Laboratory Manual* 2$^{nd}$ ed, (Cold Spring Harbor Press, Cold Spring Harbor 1989). Affinity purified anti-HMG-I(Y) IgG and purified rhuHMG-I protein was prepared as described (*Meth. Enzymol.* 304:155–88 (1999)). Electrophoretic separation of protein/DNA/antibody complexes (EMSA) followed the procedures of Kristie and Roizman (Kristie et al., *Proc. Natl. Acad. Sci. USA* 83:3218–22 (1986)). Assays were performed in 10 microliter 1 of low ionic strength buffer (10 mM tris, pH 8.0, 1 mM EDTA, 25 mM NaCl), which included bovine serum albumin (20 ng), single stranded calf thymus DNA (500 ng) and varying amounts of antibody. After incubation on ice for 15

TABLE 8

Selection of Cell pools in DHFR selective media

| Vector Passage in selective media | Days in various selective media | | | | Total cells at harvest | | | |
|---|---|---|---|---|---|---|---|---|
| | p1 - GHT | p2 - GHT | p1 MTX[1] | p2 MTX[1] | p1 - GHT[2] | p2 - GHT[3] | p1 MTX[4] | p2 MTX[5] |
| pG(III)$_4$SV40 | 18 ± 5 n = 7 | 8 ± 2 n = 7 | 21 ± 8 n = 7 | 5 ± 2 n = 7 | 9.8 × 10$^6$ ± 10.3 n = 7 | 15.9 × 10$^6$ ± 6.1 n = 7 | 10.0 × 10$^6$ ± 9.5 n = 7 | 10.1 × 10$^6$ ± 8.9 n = 7 |
| G3.8SV40 | 21 ± 5 n = 7 | 7 ± 0 n = 7 | 36 ± 14 n = 3 | 6 ± 2 n = 3 | 9.8 × 10$^6$ ± 10.3 n = 7 | 15.9 × 10$^6$ ± 6.1 n = 7 | 7.3 × 10$^6$ ± 1.9 n = 3 | 9.1 × 10$^6$ ± 4.4 n = 3 |

[1]pG(III)$_4$SV40 and pG3.8SV40 selected in 75 nM MTX.
[2]Cells seeded at 3 × 10^5/flask.
[3]Cells seeded at 1 × 10^5/flask.
[4]Cells seeded at 1 × 10^6/flask.
[5]Cells seeded at 5 × 10^5/flask.

Example 14

Cell Culture

A colony forming assay was performed as described in example 13. In this case the plasmids being tested were pGIIISV40, pG(III)$_4$SV40, pG1.9SV40, and pGBELSV40. All these plasmids are described in FIG. 4 except for pG1.9SV40. This plasmid has three copies of the III box (nt 11493 to nt 12120 GenBank sequence number AF93661) inserted in the EcoR1 site of pGBESV40. The colony forming assay indicated that the plasmids have EASE activity in the following order: pGBESV40 is less than PGII(III)

min, varying amounts of crude CHO HMG extract or 20 ng of purified rhuHMG-I were added and incubation continued for 1 hour on ice. This was followed by addition of 2 ng probe DNA and incubation for 30 minutes on ice. Loading buffer (50 mM tris, pH8.0, 12.5% glycerol, 0.01% bromophenol blue) was added and the complexes separated by electrophoresis through 6% TBE gels (Novex) at room temperature for 3 hours at 45 V. Gels were dried and exposed to either x-ray film or a phosphor screen (Molecular Dynamics) for an appropriate time. The phosphor screens were analyzed on a Storm 860 phosphor imager (Molecular Dynamics) using ImageQuant software (Molecular Dynamics).

Polyclonal rabbit antibodies against HMG-I protein used in the gel shift assays were characterized for specificity against HMG-I(Y) proteins using Western blotting techniques. The production, characterization and use of these antibodies has been described ((Reeves et al., *J. Biol. Chem.* 265:8573–82 (1990); Disney et al., *J. Cell. Biol.* 109:1975–82 (1989); Fashena et al., *Mol. Cell Biol.* 2:894–903 (1992)). The antibodies employed here were produced against recombinant human HMG-I (rhuHMG-I) protein (*Meth. Enzymol.* 304:155–88 (1999)). Western blots were incubated with a 1:4000 dilution of the rhuHMG-I(Y) antibody for 2 hours at room temperature in PBS, 0.5% Tween 20 and 5% nonfat milk (Blotto). The blot was rinsed for 50 minutes in a high salt buffer consisting of PBS, 0.5% Tween 20 and 0.5 M NaCL and subsequently for 5 minutes in PBS Tween 20. It was then incubated with a 1:6500 dilution of HPR-F(ab')2-goat anti-rabbit IgG (H+L) (Zymed) for 1 hour at room temperature in Blotto. The blot was rinsed as described above and then developed using the ECL Western detection reagent kit (Amersham Pharmacia Biotech). It was found that the antibody detected double bands that migrated at the expected molecular weight for HMG-I(Y) proteins.

In FIG. 6A, it is shown that only probes 1 and 3 bind rhuHMG-I. In addition, the DNA rhuHMG-I complex is supershifted in the presence of anti-HMG-I antibody.

To test whether hamster HMG-I(Y) binds specifically to these probes, crude CHO cell HMG extract was used in EMSA with probes 1–3 (FIG. 6B). As shown, probe 2 did shift in the presence of the extract, indicating that some of the proteins in the extract bound to DNA. The complex formed by the crude extract and probe 2 when compared with the complexes formed by the extract and probes 1 and 3, looked qualitatively different. The complexes using probes 1 and 3 demonstrated higher mobility and bound all the probes. The complex formed by the crude extracts and the three probes were further shifted in the presence of anti-HMG-I(Y) antibody indicating that HMG-I(Y) may bind directly or indirectly to the proteins binding to the DNA probes. Again, the nature of the complexes formed with probes 1 and 3 appeared to be different than the ones for probe 2 since no supershifted bands in the probe 2 complex co-migrated with the ones formed with probes 1 and 3.

Example 16

RT-PCR Cloning

The CHO HMG-I(Y) gene was amplified from complementary DNA by PCR. A primer set complementary to the middle of the murine HMG-Y gene [Johnson et al., *J. Biol. Chem.* 263:18338–18342 (1988)) (GenBank accession number J04179, 5'-AAGAGACCTCGGGGCCGAC-3') and 3' of the gene (5'-GTCCAGAGGTAGTTTGTGAACAG-3') was used to clone the 3' end of the CHO HMG-I(Y) gene. Following sequence analysis of this region, a second primer set was designed based on the murine HMG-Y gene 5' of the ATG (5'-CTGCGGAGTTCGCGACTCACT-3') and the 3' end of the CHO HMG-I(Y) gene (5'-TCACTGCTCCTCCTCCGAG-3'). Two different PCR products were obtained representing HMG-I and HMG-Y, the splice variants of the HMG-I(Y) gene. These were sequenced and the predicted amino acid sequences determined. The CHO HMG-Y cDNA sequence is deposited with GenBank as accession number AF193763, and the CHO HMG-I cDNA sequence as AF193762.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

We claim:

1. An isolated polynucleotide, comprising a nucleic acid molecule selected from the group consisting of nucleotides 11538–11692 of SEQ ID NO:1, nucleotides 11538–11760 of SEQ ID NO:1, nucleotides 11673–12165 of SEQ ID NO:1, nucleotides 11813–12165 of SEQ ID NO:1, nucleotides 11899–12165 of SEQ ID NO:1, fragments of the foregoing DNA that have expression augmenting activity, DNA complementary to the foregoing DNA, and combinations of the foregoing DNA that have expression augmenting activity.

2. The polynucleotide of claim 1, comprising nucleotides 11538–11692 of SEQ ID NO:1 ligated to nucleotides 11813–12165 of SEQ ID NO:1.

3. The polynucleotide of claim 1, comprising nucleotides 11538–11760 of SEQ ID NO:1 ligated to nucleotides 11899–12165 of SEQ ID NO:1.

4. The polynucleotide of claim 1 further comprising a recombinant expression vector operably linked to the nucleic acid molecule.

5. The polynucleotide of claim 2 further comprising a recombinant expression vector operably linked to the nucleic acid molecule.

6. The polynucleotide of claim 3 further comprising a recombinant expression vector operably linked to the nucleic acid molecule.

7. The polynucleotide according to any of claims 4, 5 or 6 wherein the expression vector is a bicistronic expression vector wherein a first exon encodes a protein of interest and a second exon encodes an amplifiable dominant selectable marker.

8. The polynucleotide of claim 7, wherein the amplifiable dominant selectable marker is dihydrofolate reductase (DHFR).

9. The polynucleotide of claim 8, further comprising an IRES sequence between the two exons.

10. A mammalian host cell, comprising the polynucleotide according to any of claims 4, 5 or 6.

11. The mammalian host cell according to claim 10, wherein the host cell is a CHO cell.

12. A method for producing a recombinant protein, the method comprising culturing a host cell of claim 11 under conditions promoting expression of the protein.

13. The mammalian host cell of claim 10 wherein the recombinant expression vector is a bicistronic expression vector wherein a first exon encodes a protein of interest and a second exon encodes an amplifiable dominant selectable marker.

14. The mammalian host cell of claim 13 wherein the host cell is a CHO cell.

15. A method for producing a recombinant protein, the method comprising culturing a host cell of claim 14 under conditions promoting expression of the protein, and collecting the protein.

16. The method of claim 12, wherein the protein is an antibody.

* * * * *

SEQUENCE LISTING

<160> NUMBER OF SEQ ID NOS: 1

<210> SEQ ID NO 1
<211> LENGTH: 14507
<212> TYPE: DNA
<213> ORGANISM: Cricetus griseus

<400> SEQUENCE: 1

```
gcggccgcga gctctaatac gactcactat agggcgtcga ctcgatctcc agggtctaag      60 gacccactt  gacgcaatga  attttgtttc  aggataagct  agaagccaga  agctgctaaa    120
gaaagttacc  atctgttaaa  aactgcagcc  aagatttgtt  gtttgtttgt  ttccgagaaa    180
gggtttctct  gtgtagccct  tgctgtccag  gaactcagag  atccacctgc  ctctgcttcc    240
tgagtgctgg  gattaaaggt  gtgtgctgac  tacaggcaag  cttgtttgtt  tatttgtttg    300
tttgtttgtt  tttcaagaca  gggtttctct  gtatagctct  ggctgtcctg  gaacttgctc    360
tgtagaccag  gctgtccatg  aagtcacaga  gatctgcctg  cctctgtctc  cctcctgagt    420
gctgggatca  aaggtgtaca  ccatcaccca  gtccccactc  cccccccac   ctcccagcac    480 aggcaaggtt  tttaatgtat  agactctgca  taatattcca  gttcctttgg  ccatatatac    540
```

-continued

```
aaggatggaa aaaatacctg aaaataatgg ttttattttt ggtcatggaa ttttaataca    600
ttttctttta ttcatttcag tgtctttcaa atcctaacat tttggctaca gaattaaaaa    660
aaataataac tgaccttaaa cttccatgtc tgtgataagg tacatttgt  tattattgga    720 ggataaactg ttacttcacc aaatgttact tgtaaatgtg ctgttcacca tgcatctggc    780
tgcagtttct ctaggccctt tggcctattg attgttgtct gcttcttaag ttagctccta    840
ggacctctgg acagcctcat ctggagctgc ggctgctgtt gcccttcctc tgtagctgtc    900
catgttgcct ctgcagtatt tgctttcctt gtccttgttt gtgctgttca ttgctagttg    960
tactccaata tgcaaatttt tgaaaacttt ttcagtaaca ttatcctaat tgttcctttt   1020
cgtttataag tagtttactt tctttacata attttcttag gactgatgca tttcaattgg   1080
cttttttttg tgacagggtc tcttgttgct caggctagcc ttgagctccc agttctcctc   1140
aaatcctcaa actttatggt aaagaagacc taagtttatc atgggcagcc atatatgctg   1200
attatccttt ccttataata tataatattg ttattcatgt agaaggagct ctttaatgcc   1260
attttgttaa acagccaact atttagcata ttagctgttc atattttata gttttttaaga  1320 gctcttttt  gggatcatta tgaatttata gagaaaagtt tggtttaact agttagccat   1380
agaaatggat agactattca gttggatagg aagcagtatg ttacttatgc tgtcataatt   1440
gcagtgtaca agaacccagc aaaatggtag tggtgttggg gaggaaaagt gacaacattg   1500 actcttggt  ggacagcaga gcatagctat attatttggt ttttcgagat agggtttctc   1560
ttgtagcttt ggagcctatc ctggtactcc ctctggagac caggctggcc tcgaactcac   1620
agagatccgc ctgcctctgc ctcccaagtg ctgggattaa aggcgtgtgc caccaacgcc   1680
tgacattaag ttttctgaca ctgtcaggaa ttgtcacttc tgcttctcag tttccttctc   1740
tgaaaaatga ggagaaaggt atctaggctg cctcctcatt tctgactagt tttgtttgtt   1800
tgttttgaga cagggtctct ctcatttggt agtcttggct ggtgtggaac caggcttatc   1860
ttgaactcac agagatccat ctgcttctac gccttgaatg ccgggattaa aggatgtgca   1920
taatttatag actagttta  ggaagggaaa aaaaaagac  tatggtagaa gaattgtgg    1980 aagtgtttta ttatacctga aagtcctttg tggcaatttt ggcatggtta ggcaaagttt   2040
aaacatccca gtcatcaaat agattacatc acgacattcc tatggcttat cccggactca   2100
taaaagtatt ttatgattca cttaaagatt taatagtgat ttggattact tgtgtgggaa   2160
aacacaaaat gaggctgtag tatcttacag tgtcagaaac aatactttaa aaacctactg   2220
ggatcctgtt agaggaccct taaagaggcc ccactgggca gagctagaat cagatgagcc   2280
acgagagaag gaatgtggac tattgctttt aagtatgaag tgagcccaca tctctgctat   2340
aaatgatata aatgaatggg ggggtagtct accttatgga agaactccaa aactttatgt   2400
agctcttgca acttcatgga gaaagtgaag tatggtatcc tgaactggga tctagaatac   2460
aaagatgaca tgtgcagaaa gcattctaaa gtccaagtga agtttggagt ttaaccaatg   2520 ttaatttta  attttgacaa gtgtaccatg gaaataaaaa atattaacag ttgggggggag  2580 ggagctagga gaatgagaag gggaaaagag gagggtgtg  gaggacatga gggagcagaa   2640
aggttgagtc aggggaagaa tagaagataa caagaatgga gataccataa tagagggaga   2700
cattttagga ttacagagaa atcaagaaac tagggaaatg tctggagatc tacaaagatg   2760
acactagcta acaatctaag caacagagga gaggctacct taaatgccct cccctgataa   2820
tgagattgat gactgactta tatgccaccc ggcacccaca actaatcact gaactgaact   2880
ggaatccagt tgcagagaaa gacaagtgat gaccaggctg gtgaaaccca cagaaacagc   2940
```

-continued

```
tgacctgaac attggggagc tcttggtccc cagactgaat gctgagataa cagcatggga    3000
ctgatccaga ccccagaaac atgggtttca gtgaggaaac cttggaaatc tacgggacct    3060
cctgtagtag ttcagtactt atccctagca taggtgtgga gtttgggagc ccattccaca    3120
tagaggaata ttacctgagc caagacacat ggggtgtggc ctaggccta tcccaataga     3180 ctctgatgac accctattta aagcctcacc atccaggggg agcaggaagg atatgtgata    3240
ggtagggttt tagttggggg tggtggtggt aagggaggat gggtgggtgt gggaactggg    3300
attgtcatgt aaaacaatct tgtttctaat tcaaataaaa tctacagaaa aaatagtaac    3360
agttgggaaa atgagtaaga agtagtcagg atctttctat tctgagatta agtttaccc     3420 ttttagaaaa ggctggggat ataacttagt ggtagagtgc ttgccttgca tgtccaggtc    3480
cctaaattca agccccagta ctacagagat acatacatac atagaagatt taacagactg    3540
tgcttgcaga cccagtttca ttttagccag agatatagtg aaactctatc tcagtatgtt    3600
cctatcaccc gcatggttag aaatagttga ttttaaatat aaaatctaag tgaacttgta    3660
gagaatatga ggaattaaaa gtagaaggtt gattttggtt caagggatt tccagttccc     3720 caagtggtac aagatgtttg caaggggca cagtaaagaa actgtgctga cataaacaca     3780
ctatgatatg ataactgttt ttattgtagg gagagagag agaggagaga gagagagaaa     3840
gagaaagagt gatttaacaa gtacttgtga tactgaagga gcctggaggc tgtcatgggt    3900
tttgatatgc aatcacaggt atatatcagt ggagagccat atgtaccttc tgccagaggt    3960
aagggtaagg aaaatgagtc attttggcag actgaaactg gtttcccaag ttcctgagaa    4020
attctggtgt ttaactacca gaaattctat agtctggctt gagttcattt ctgggtatac    4080
agactgcctt ttggagtttg ggatttggag tttatttcct ttggactgac agttgaaaat    4140
acaaatcacc tcacttggtt atcatctttg gattttgact gcttttaga tgaaacttgt     4200 tcccatgacc atgcagacat cattatggtg tgtatgtgta tatgtaatta tgatgctgta    4260
tatactcagt tttgtagatt taattttaac tatgtatttt ccaagattta attttaacta    4320
tgtattttcc agtccacaag taattattag actactttat ggaccagata ccaagataag    4380
tacacttggg ataatggatg agtgagaatg ctgtgggtct ttgtttggag ttgttgata     4440 tctagggaga gatgatgtac tatctaggga tgatgattgt gagagcatgt aaatcgtaga    4500
accaatgaca tgtctgtcct tcaaggcaag tgaaagaagg aagcagtaga ctggtgcaat    4560
gggagctgga atacagtgtt cacttggagg cagagcatca gctagtgctg aagcctcata    4620
gtgtgaagcg ccaggagga acagtgtctg gagtgcagag aatgggcctt tagaaaggaa     4680
tagccagaga ctgaagaaat agcaaagtaa gagcttaatc atgaaactta gcctgggcgt    4740
tcccttgaaa gtgatggaac tcactgagaa tactaaagct aggcagtgat aaaaggagcc    4800
tgctgtggtg tgggcaaata gatgggcaag tggtgagaag tcctggacct ggtagtgtgt    4860
taaaagtgat agtaaaatac aagctgtttg taattgctgc ctgctgggaa aggaaaaagt    4920 cactttttc cccaatggag tgtcaatggg tatatcaact acactccaca aaatgaactc     4980
catgaaattt ttatgggctt tttgttttat ttgttttgtt agagagagag agagatagag    5040
atagagagag agagagagag agagagagag agagagagag agagagagag agagagagag    5100
gagaaagagg cctttagaga gacaattaat tttgggtttg tggtgaggta gggaagatct    5160
gggaagagtt ggggaggaga aaatatgacc aaaatatatt gtatgaaaac aagatattgt    5220
aaaacaggag attattgcta gaatataaca gttgaaatgc taggagttgg agttggttgc    5280
```

```
ttttataact gataatgaag ttgggtgttc ctacctcagg taaaaaaaac tccagcacag      5340
taatccaaga gtagccattt gtacagtgtc cttgtttgta gttttaagag caaagaaat       5400 tgttttgtag tagaaagttg tggtgttgct cagaaaccaa ataaaggaat tctgagttag      5460
aatcttttta tttggcaaca gcatgctgac tgtgagagat acaagctgc ttttgactgt       5520 attgttttac ttggtatcca ccaatagcat tggtggtact attctactga gatgtgccag      5580
caccatgtca cattgggtac cataaactca ctagccatac attgagaatc tttgggaaag      5640
gctggtttag aagctgtgat gactattctt ggttgtcaac ttaactatat ctgcaatgaa      5700
ctgtaaccca gagatggagg gcacacacat gatccggatc ttgagactgg ttgacacgtc      5760
ctttaatcca gcccttgctt gaggctggag ggtacacctt taatctggct acaccttctg      5820
ctggaaggac aattgaggaa agaagggggtg tgtttgttct tggcctgttt tccctcgtct    5880
tgtcagcaca tccatttctt tcactggtat tggagtctac ttctttggga ttttatcata     5940
tacagaagac cagttgagat gctgagtctc ctgggactgg atccttggac tttttattca     6000
caggtaggca ttgttggact gcagccctta agtcattcca atatgggaat atatatattc     6060
taaaagttat atatgaatga atatatatat tcattctata agttctgtga ctctaagaga     6120
cctgactaat acagaaactt tttaaacact tttagttttt cattgtatgt atgttttgta     6180
tgtgcttgtg agtgcagatg ctcatggctg cagaggtatg gagtccctac agtatttaac     6240
attgttaaat ttcttttcct gctttcacca ctacttctgt cgttaactgg cttgttgtga     6300
taggtggctg tccagttag ggtggctatt gctgtggtga acaccatga ctaaagcaac       6360 ttggaggaaa gggtttgttt gactcacaat tttatgtaac agtccatcat tataagcaat     6420
gagagtagga cctcacacag ggcaggacct ggcagaaccc atggaggaat gctgcttact     6480
ggcttgttcc ccatggcctg ctcagcatga ttacttatag aacccaggac caccagctcc    6540
agtatggccc cacccacaat gggttgagtc cccccacggt aaccactaat taagaaaatg     6600
ccctacaagc ttgcctatag cccaacctta tgaaggtatt ttttcatgtg acaaggtgac     6660
ataaaattag tcagcacagt ggccaagcct gtatctttga gactcccagg ccccagcttt    6720
gcctaactgt atttaatgtc tgcctgttgg agagaagtcc agatgctttc aaatggtcta     6780
ctcagactta ttttttagaaa taaactattc caaagttcat ctggtactta ttctaagcaa    6840
ggtcatgctc ttcatgcatt tgatagcctt cacctgttg tcagttccct tgtaaacatt      6900
ttctgcaccc atatccccag gctgtttatt tagagcaacc tacttaatgc tagtagaatt     6960
agaggaccgc ccaaatgggt gcattcatgt aacaggaagg tggtacattc agagaaaatt    7020
aaaatacgtt aaatttatgc agtgctgtga tttgaatgt tttaaatgta ctaggaaaaa      7080
gaacttggag atctgttggt tcctgcctgg ataaaatgag cctaagtacc aatgaaatcc     7140
tgaaaatacc gaattggtat tactggaaag aagtgtttgt ttttttattac actactggac   7200 ttggctattt gtatctaaaa tcccatctgc aaatgttgcc ttagcacagt aaaacagtaa     7260
ggtattgaaa aggttcaaaa aagtgcaagt cattgaatac tgtgttatat ttgctctacc     7320
ccttggttag gtgtgaagga gtgagcataa caaatcctaa gtgagtgagt cagttgtctg     7380
tttttctgtt gtgtatttgt tttgtgattc ttgatttctt taaaagatttt tatttattta   7440 ttgtatacaa cattctgctt ccatgtatat ctgcacacca gaagagggca ccagatctca    7500
taatggatgg ttgtgagccc ccatgtggtt gctgggaatt gaactggga cctttggaag     7560 aacagtcagt gctcttaact tctgagccat ttctccagcc ccgtgattct tgatttatc     7620 ttctactttc tgcagaaaat attttaaaac tggaattaga tggtttggct ctttggcttt    7680
```

-continued

```
ccattccaat tgagtacatt taaggctgta aatttccctt taggtaatat tgaatcttta    7740
tgctgttatc tttagttatc atcatcattg ttattttacc ttttacaata gtatttactt    7800
tagtggacat gaccaggctg agctgggcta tgtgggacag ggaggggagg ggagagagga    7860
accaactgca gcacccagga ggccaaaggg acaagaggga aagggtggg taaccaaaat     7920 gtctggtttg tataggaaaa agctctggag gaagggtggg gaatgacagc cataccttgg    7980
aacagttagg gactgaggat gctggaagaa cctgttggcc atatctagct ttaatatgtt    8040
aaataggcac ctcagctgtt tgtcctggat ttgaaattta acaaaaagat agtagttttc    8100
ttaggtcatt agtgttatat gtgaccagga ggctggagca ccacaatatc acaatacaaa    8160
taatctggtt tagccaggct tccatatgag gttgatgttt gactagaaaa gggtttgcaa    8220
gccctgtgtg ttacctcctg gcttgtgatt ttggttcttc agagtttccc ccttaagcct    8280
taactgcttg ttgtgttcaa gaattcagga ctttttagcca ggcttggtgg caggaggcag    8340
aggcagtcgg atctctgtga gttcgaggcc aacctggtct acagagcaag ttccaagaca    8400
gcctcgcaag ctacacagag aaaccctgcc tggaaaaaca acaacaacaa caacaaaaac    8460
aaaataaaag aatgggcagg ctttgaggtt tccagtgctg acatactgtc cagtgtctca    8520
gttgatgtct tgttgcctac aaaatgtaag aactctcagc tcctccagca ccacgctgcc    8580
atgtctcgcc atgatgacaa tgaactggac ctctgaaact ataattgagc cacccccaatt   8640 aaatgttttc cttatatata taaaaaaaaa gaattctgaa cttttctttt gttcccttcc    8700
cttctaccac accctaattg taatccattt taatttcctg gtcacagtcc tgtctctcct    8760
tccattgtac cttgccctt tctaaagagc gactgcaaag tatgtttgcg taggtgagga     8820
tctaaaactt tatgaggtac gaacatcaca gaattacttt gtaatttcag tttattgtag    8880
gcttggcttt ttggggaggg tttacgtctt agacctctta gtgcttcttt gtttcatggt    8940
gttctaactt cgaagcatct ctgtagcttt aatggattcc ttttctgaaa gctttgctct    9000 cttcttccc cctcggcttt ctcttaggca agagggctaa ctgtaaagta aggcttactg     9060
ccttgtgttt ccaaatgtgt ccgaagagga agtgtcttct gtgaatcctg ttatgcatga    9120
ataacaggaa atagaaagaa attcacttc attattataa aagtaatatg ttcgtttaaa     9180
aaattctaat gaagagctgg agatgcaacc caggggtaga gcacacactc agcatgcagg    9240
aggccctggg tccaatcttg gaatctcctc tcagttaacc tgatctctag ctgattagta    9300
gtgagtgcaa gcccactttc ctcttctgcc tcattgctca gtgataacag ctgttaaact    9360
ttgtcttatt ctaaaactac ctctgtgcaa atgctagcac aataatatat atcatatgca    9420 catgatttt tttttatctt gaaaagtaag tcagtatagc tacaaagttc acttggcatt     9480
gtcaacattt cacaggcgta atattcctcc tctagtactg tcctcttcat tctttgtgac    9540
caagtttgga gagagtgcac aaatgccagg gaggtttgtg ggaaggtttc tcatgttctg    9600
gtaaggcgag taagaaaata gtctcatgca ggtgaaatga gtgctatgca gtatatatta    9660
taccagagaa cagcaaatga ccaaattcac actgaactag ttcagtaaaa ttggctttgt    9720
caaagctttc cttgcttaaa atgtaattcc ctgtcatcct agttctggtc tggattcttt    9780
tcctggagtc ttgacttcca gattcccgtg tggacttttgt ttgagtttca agcttttgaa   9840
atatagaaac ctatctaact taacaaactt gggagagaaa agactccaga acaactgaaa    9900
acagaccagg ctaaatgaat agactttatt cctctcttct tacctgcagt tttcagatat    9960
gcagagttgg agcggatctt agaggttgat tcattcatgc ctgaagaaaa cacattttat    10020
```

```
agaccctgtg cccaagttcg tggtggacat caccctttat ttactaattg cactacataa    10080
caggcatttt agaagactgc tccagtcaga gaccccgcct tagaggaatc tgtaaaccct    10140
gaactcctat cactcatgag cactagttat gtttggaatg ccgtattaaa acaaaagtta    10200
catttctaaa cttaaaattt tctagcacag agacagtggg agtagctaac tttgatagac    10260 attttttctac taaaagtctt tctaagtaca taatcttctg taagttggaa acagcaaaa    10320 tagaacgtct cctacgtagt taatctttttt gcataatttg cacatgtagg agttattagt    10380
atacgggtaa gttttcactt tttcccccaa ctggagtgtc ttgtggctgg gtttgaaaaa    10440
gggaacggga ggccgctgga ggggattggt aaatgagata aaacaccact cattcaactc    10500
agtgactcag catttaaatt ttccataaaa ggattaaagg aaaattaaac aaattcttaa    10560
agccaagact ctggagaaac ttgttggtgt gctttagttt tcactgttat gactcatgaa    10620
tttatgcata aattagtaca tttataaaaa catagccttt ttagagtttt ctgtttggct    10680
aaagtgccat tgttagcatt tggaattacc tttttatgtc ttatatttttt tccaaataaa    10740 aataaatgtt tctgctgtct tactactgaa actacgttgt gagcacttta aatttctcaa    10800
agcagtttcg cctgttatac ttggcgctta gtcatcgtcg tacacaacag gacctgatta    10860
agaaggctgt gctgcctcta agccgggcta gattgtagcc actagcaacc aggctgcaat    10920 aatttcccctt tgatgacatc atccactgtg gaagaaccca gttgcttcag ccagtcgaac    10980
tatacagttc caacctcatc aaatatggca tctcccttgc ctgctatagc agggggagga    11040
aaaaatgcca ccatcttttt aatctagcaa gcttctcttt tcttcatctt ttttttttttc    11100 ttttaaaaaa attctgatca tggatgcttc ttccgatccc tatttgcctt atgacggggg    11160
aggagacaat atccccttga gggaattaca taaaagaggg aagagcatcc ccttgctctg    11220
aatcctctgt tggttgttgt gcatgcggct gggcggttct ggggacaggc tgtctgttgt    11280
cctcttgctg caatgtgctg cttagttgcc ctgccttgtt gctgtgggag aatgcgacct    11340
tcccagcagg gctggccctc cctgattgtt tgctctgtgc agattagccc tgcttcagat    11400
cacatagggc tgcagactcc atcttctgtg tgaaaatgct ttcggtttga ttgcagaaat    11460
aagctgcctt tacagccagc taaagtcctg gtggttggtt ggcacctgca agtagtatt    11520 tttgtacctc tggaaactta tattttcttt acacagcaat atcaagtgcc ggtatgccat    11580 tctgtttttgg ctgctgccaa ttaccatgta gactttgcac cacagagtaa tagtaaaagc    11640
tcctagctgc attttataac atttaaaaat agcaggaaag aagaattatt tttgatttaa    11700 catgttttttg tcatttaacg tcttaactga ttgacatact atattgtctg tctcgtgggt    11760
atcttgtaca acttgatagg ataaagcaat ttagtttttt ttttttttttt taaatacatc    11820 cagaatgtaa gtcgtcagta gttttcgaac agataagtaa tggtgttaat cttttggcag    11880
gctttgcctt ggtctcctta aagctaatta ggtgttactt aattaaactg ctcttttgct    11940 catttctta aattattttt ttaaaagata gttggcattt gctgttctag aaataaactt    12000
caagaaacat tctttagcca gatgacttca tgtatgagcc atgttagttt gaattatttg    12060
cttggtgtta taaactttat ggtttaatac caacttttat tatgtttaca aggtaaataa    12120
ggaaaatttc aagtacattt tgtatcctga gaacaaattt aagttccata gaatttagga    12180
attacaatgt attcaacaga tacttacttg tcatactgtg cctgcaaaac aataattaga    12240
ctctgaacag gtgcaacaat tttctgtaga attctgtgct tagtaaaagg ttgctttttta    12300 tattttgaga gaaatctatt taaagatcat ggcccatatt ttgtgcatat ttttttctgt    12360
ataccatttc catatatgtg tgtgtgtgta catatatgta tatatataaa atgttagaac    12420
```

```
atttgaggaa atagctaaaa gtacaaaagt aatgttttct aattttttac tccccgaggt    12480
tatttctttt ttccttgttt tcctttctct ttgttcctat catcagtttc tagtaatact    12540
cttattgaac agtgattatt caaatgtcac attatttatt aatcagcatt taaatggtaa    12600
aaccagacag accatacttt ctctgagtga tgacaacatc cattttagt aatgataaac    12660 tagaagggtc aggcttgata gtctttgtca ggactaattt atagactgta aaggccaaaa    12720
gaaataagaa atgtcaaaac tcttgtgaaa ctagacatac agatattacc aagagagaaa    12780
ctagaaaaaa aaattctgtg acatggcctt aatttgccag gcaccatcgt gaaggcctaa    12840
acccctctta gaagctcact cagatgccat cctgcttctc tgatgagact tcctgtcaat    12900
acaaacatgg tttaggaaga atgagtgttt gcagtataaa ccagttattt actagcctta    12960
ctttaagaat atactgtagt gtccttgaga gagaaggtgt ttgttttctg taatttatga    13020 ccctttgaa accatagatc agcacaaagg aactggggat atggaaatgg gaacataact    13080
taaatccaga aaagtgaatc agattccctg tgaggacaaa atgcaatatt tagaaatagg    13140
atctttaggc tgggagggag aaaagaggaa aaaaatgaaa gtataacatt tttcataagt    13200
ataagatttc ataaaaaaat gaaatctata acatagaggg tgttgataaa gtaagcatgg    13260
atatgtttag taaagccgac agagctaaga attagctttg tgagtaattg gacttaatca    13320
aacttttcaa ggtgggatac aaatgaataa ttgtagaata aatggataaa agaatatgaa    13380
taaaatgaat agtgagtaaa aattaaaaat gaagcttttt acttaagtgc atattgtagt    13440
ggctagaaca aatagattca aaatagaaat catttatata ttcttgatta gaagataaaa    13500
tgttatttta gaaatagcca tctttggaag taaatttgct atgttgaaca accaggtttt    13560
cataatttgt ctcttatttt ttttcaggaa gaaaaaaaaa cttgacttat ttgtactgct    13620
aagttttatt caatgtgctt gcttgcttaa attttttaatg aagttttagt catttggtgg    13680
tcaaattcct tttatctact aatcgctttt cgtggctttg cttttaaaa ttgtatttac    13740 tgcatttatt tgtgtgtatt aggagtcagg tggccatatg tgccatggca tgtgtatgga    13800
agcacttgtg gacatgaatc ttctctttcc acatgtgtgg gccactggaa tcaaactagt    13860
gtcaggcttg gcagcaattt ttaatgcact gagccttctc accaccccct ggacttttgt    13920
ggggcagaag gggacaagtt taatatttta tttactccat gtagaaagcc tttaaaaaat    13980
gtagaaagcc tttaaactac ctattgtttt atttgaatta tgaagctctt gtgtttatat    14040
aaattacagt taggtactgt ggagactaat ggtagctaca atagtaatat taatagctaa    14100
aacttagtag aatctgattg agttaatttg gccctttcca tcataaggta ctcttcccaa    14160
gcatcacatg acctgtgctt aagtctggtg ggggcttatg gctttgatat tgaaaacaaa    14220
tcgtcaagga tgttaatttc ttgttactgc tattacactg aattttctat ggctctttag    14280
gagaggaaga gacaagtctt cttttggcag gtgttactaa gtaggccatt tcccaaggaa    14340
cagggaattt gccaggcttt tgtggtggag agaatagaat gaataaatgc tgtgggagt     14400 aaagagcttg tcagaagatg attagttctg tggcaccaaa accaagagat cagttttcct    14460
gtgagaagta aaggaagcat tgtagaaaaa tagatgtgtt gaagtct                 14507
```